US010786446B2

(12) United States Patent
Ma et al.

(10) Patent No.: US 10,786,446 B2
(45) Date of Patent: *Sep. 29, 2020

(54) MULTI-LAYER HYDROGEL CAPSULES FOR ENCAPSULATION OF CELLS AND CELL AGGREGATES

(71) Applicants: Massachusetts Institute of Technology, Cambridge, MA (US); The Children's Medical Center Corporation, Boston, MA (US)

(72) Inventors: Minglin Ma, Ithaca, NY (US); Daniel G. Anderson, Framingham, MA (US); Robert S. Langer, Newton, MA (US); Omid Veiseh, Bellaire, TX (US); Joshua Charles Doloff, Quincy, MA (US); Delai Chen, Woburn, MA (US); Christian J. Kastrup, Bowen Island (CA); Arturo Jose Vegas, Belmont, MA (US)

(73) Assignees: MASSACHUSETTS INSTITUTE OF TECHNOLOGY, Cambridge, MA (US); THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/200,334

(22) Filed: Nov. 26, 2018

(65) Prior Publication Data

US 2019/0091139 A1    Mar. 28, 2019

Related U.S. Application Data

(60) Division of application No. 14/776,639, filed as application No. PCT/US2014/029189 on Mar. 14, 2014, now Pat. No. 10,172,791, which is a continuation-in-part of application No. 13/831,250, filed on Mar. 14, 2013, now Pat. No. 9,555,007.

(51) Int. Cl.

| | | |
|---|---|---|
| *A61K 9/00* | (2006.01) | |
| *A61K 9/48* | (2006.01) | |
| *A61K 9/50* | (2006.01) | |
| *A61K 35/39* | (2015.01) | |
| *A61K 45/06* | (2006.01) | |
| *B01J 13/04* | (2006.01) | |
| *A61K 35/12* | (2015.01) | |

(52) U.S. Cl.
CPC .......... *A61K 9/0024* (2013.01); *A61K 9/5036* (2013.01); *A61K 9/5078* (2013.01); *A61K 9/5089* (2013.01); *A61K 35/39* (2013.01); *A61K 45/06* (2013.01); *B01J 13/046* (2013.01); *A61K 9/4833* (2013.01); *A61K 9/4866* (2013.01); *A61K 2035/126* (2013.01); *A61K 2035/128* (2013.01)

(58) Field of Classification Search
CPC .. A61K 9/0024; A61K 9/5036; A61K 9/5078; A61K 9/5089; A61K 35/39; A61K 45/06; A61K 9/4833; A61K 9/4866; B01J 13/046
See application file for complete search history.

(56) References Cited

U.S. PATENT DOCUMENTS

| | | |
|---|---|---|
| 4,352,883 A | 10/1982 | Lim |
| 4,391,909 A | 7/1983 | Lim |
| 4,407,957 A | 10/1983 | Lim |
| 4,409,331 A | 10/1983 | Lim |
| 4,673,566 A | 6/1987 | Goosen |
| 4,689,293 A | 8/1987 | Goosen |
| 4,744,933 A | 5/1988 | Rha |
| 4,749,620 A | 6/1988 | Rha |
| 4,806,355 A | 2/1989 | Goosen |
| 4,868,121 A | 9/1989 | Scharp |
| 5,273,904 A | 12/1993 | Langley |
| 5,322,790 A | 6/1994 | Scharp |
| 5,427,935 A | 6/1995 | Wang |

(Continued)

FOREIGN PATENT DOCUMENTS

| | | |
|---|---|---|
| WO | 9219195 | 11/1992 |
| WO | 199823226 | 6/1998 |

(Continued)

OTHER PUBLICATIONS

Paul A. Webb. Interpretation of Particle Size Reported by Different Analytical Techniques. Micromeritics Instrument Corp. 2019. 10 pages (and references therein). (Year: 2019).*

(Continued)

*Primary Examiner* — Robert A Wax
*Assistant Examiner* — Olga V. Tcherkasskaya
(74) *Attorney, Agent, or Firm* — Pabst Patent Group LLP

(57) ABSTRACT

Biomedical devices for implantation with decreased pericapsular fibrotic overgrowth are disclosed. The device includes biocompatible materials and has specific characteristics that allow the device to elicit less of a fibrotic reaction after implantation than the same device lacking one or more of these characteristic that are present on the device. Biocompatible hydrogel capsules encapsulating mammalian cells having a diameter of greater than 1 mm, and optionally a cell free core, are disclosed which have reduced fibrotic overgrowth after implantation in a subject. Methods of treating a disease in a subject are also disclosed that involve administering a therapeutically effective amount of the disclosed encapsulated cells to the subject.

20 Claims, 9 Drawing Sheets

(56) References Cited

U.S. PATENT DOCUMENTS

| | | | |
|---|---|---|---|
| 5,447,863 | A | 9/1995 | Langley |
| 5,516,527 | A * | 5/1996 | Curatolo ............ A61M 31/002 |
| | | | 424/451 |
| 5,709,854 | A | 1/1998 | Griffith-Cima |
| 5,821,121 | A | 10/1998 | Brothers |
| 5,912,005 | A * | 6/1999 | Lanza ................. A61K 9/0024 |
| | | | 424/422 |
| 6,129,761 | A | 10/2000 | Hubbell |
| 6,858,229 | B1 | 2/2005 | Hubbell |
| 8,815,283 | B2 | 8/2014 | Stover |
| 2002/0098559 | A1* | 7/2002 | Opara ................. C12N 5/0677 |
| | | | 435/178 |
| 2004/0185083 | A1 | 9/2004 | Dionne |
| 2009/0214660 | A1* | 8/2009 | Vasconcellos ....... A61K 9/5036 |
| | | | 424/490 |
| 2009/0269313 | A1* | 10/2009 | Nadler .................. A61K 35/39 |
| | | | 424/93.7 |
| 2010/0305696 | A1* | 12/2010 | Mao ........................ A61L 27/18 |
| | | | 623/8 |
| 2011/0111033 | A1* | 5/2011 | Stover ................. C08B 37/0084 |
| | | | 424/487 |
| 2012/0213708 | A1* | 8/2012 | Anderson ............ A61K 9/0019 |
| | | | 424/9.2 |

FOREIGN PATENT DOCUMENTS

| | | |
|---|---|---|
| WO | 2000012066 | 3/2000 |
| WO | 2001009342 | 2/2001 |
| WO | 2007038029 | 4/2007 |
| WO | 2009085850 | 7/2009 |
| WO | 2012121874 | 9/2012 |
| WO | 2012121878 | 9/2012 |
| WO | 2014153126 | 9/2014 |

OTHER PUBLICATIONS

A Guidebook to Particle Size Analysis. Horiba Scientific. 2019. 32 pages. (Year: 2019).*

Baruch et al. Alginate-PLL cell encapsulation system Co-entrapping PLGA-microspheres for the continuous release of anti-inflammatory drugs. Biomed Microdevices (2009) 11:1103-1113.*

Ma et al. Core-shell hydro gel microcapsules for improved islets encapsulation. Adv Healthc Mater. 2013, 2(5):667-72.*

Linetsky, et al., "Improved human islet isolation using a new enzyme blend, liberase", Diabetes 46(8):1120-3 (1997).

Wisniewski, et al., "Characterization of implantable biosensor membrane biofouling", J Anal Chem., 366(6):611-21 (2000).

King, et al, "Microencapsulation of islets of Langerhans: impact of cellular overgrowth", Upsala Journal of Medical Sciences, 106(3):161-174 (2001).

Choi, et al., "Core/shell Macrobeads for the protection of Islets from Immune System Rejection", Journal of Bioactive and Compatible Polymers, 21(1):71-81 (2006).

Piskounova, et al., "The Effect of Mixing on the Mechanical Properties of Hyaluronan☐Based Injectable Hydrogels", Macromol. Mater. Eng., 296:944-951 (2011).

Baruch, et al., "Alginate-PLL cell encapsulation system co-entrapping PLGA-microspheres for the continuous release of anti-inflammatory drugs", Biomed Microdevices, 11:1103-13 (2009).

Bratlie, et al., "Materials for diabetes therapeutics", Adv. Healthc Mater.,1:267-84 (2012).

Calne, et al, "Stem cell and gene therapies for diabetes mellitus", Nat. Rev Endocrinol, 6(3):173-7 (2010).

Devos, et al., "Factors influencing the adequacy of microencapsulation of rat pancreatic islets", Transplantation, 62(7):888-93 (1996).

Field, et al., "Improved islet isolation from rat pancreas using 35% bovine serum albumin in combination with Dextran gradient separation", Transplantation, 61(10):1554-6 (1996).

Granchi, et al., "Silicone breast implants: the role of immune system on capsular contracture formation", J Biomed Mater Res, 29(2):197-202 (1995).

Kim, et al., "Generation of core-shell microcapsules with three-dimensional focusing device for efficient formation of cell spheroid", Lab Chip, 11(2):246-52 (2011).

Kvist, et al., ,,Biocompatibility of electrochemical glucose sensors implanted in the subcutis of pigs, Diabetes Technol 8(4):463-75 (2006).

Linetsky, et al., "Improved human islet isolation using a new enzyme blend, liberase", Diabetes 46:1120 (1997).

Ma, et al., "Core-shell Hyrdogel Microcapsules for Improved Islets Encapsulation", Adv Healthcare Mater., 2(5):667-72 (2013).

Ma, et al., "Development of cationic polymer coatings to regulate foreign-body responses", Adv. Mater. 23(24):H189-94 (2011).

Orive, et al., "Cell encapsulation: promise and progress", Nat. Med., 9(1):104-7 (2003).

Park, et al., "Biocompatibility issues of implantable drug delivery systems", Pharm Res., 13(12):1770-6 (1996).

Paul, et al., "Microencapsulated stem cells for tissue repairing: implications in cell-based myocardial therapy", Regen. Med., 4(5):733-45 (2009).

Read, et al., "Local endostatin treatment of gliomas administered by microencapsulated producer cells", Biotechnol., 19(1):29-34 (2001).

Remes, et al., "Immune response in biocompatibility", Biomaterials, 13(11):731-43 (1992).

Vaithilingam, et al., "Islet transplantation and encapsulation: an update on recent developments", Diabet Stud, 8(1):51-67 (2011).

Van Der Giessen, et al., "Marked inflammatory sequelae to implantation of biodegradable and nonbiodegradable polymers in porcine coronary arteries", Circulation, 94(7):1690-7 (1996).

Ward, et al., "A hook-traction technique for Norplant removal", Obstet Gynecol 86(5):848-50 (1995).

Williams, "On the mechanisms of biocompatibility", Biomaterials, 29(20):2941-53 (2008).

Wisniewski, et al., "Characterization of implantable biosensor membrane biofouling", Fresenius J Anal Chem 366(6):611-21 (2000).

Yin, et al., "Microcapsules with improved mechanical stability for hepatocyte culture", Biomaterials, 24(10):1771-80 (2003).

Zhou, et al., "In vivo reprogramming of adult pancreatic exocrine cells to beta-cells", Nature, 455(7213):627-32 (2008).

Young, et al., "Encapsulation of Plant Growth-Promoting BActeria in Alginate Beads Enriched With Humic Acid", Biotechnol. Bioeng. 95(1):76-86 (2006).

* cited by examiner

Solution containing therapeutic cells/cell aggregates

Core solution containing therapeutic cells/cell aggregates

NT = Non-transplant background
MT = Mock transplant

MULTI-LAYER HYDROGEL CAPSULES FOR ENCAPSULATION OF CELLS AND CELL AGGREGATES

CROSS-REFERENCE TO RELATED APPLICATIONS

This application is a divisional of U.S. application Ser. No. 14/776,639, filed Sep. 14, 2015, which is a National Phase application under U.S.C. § 371 of International Application No. PCT/US2014/029189, filed Mar. 14, 2014, which is a continuation-in-part of U.S. application Ser. No. 13/831,250, filed Mar. 14, 2013, now U.S. Pat. No. 9,555,007, issued Jan. 31, 2017, which are hereby incorporated herein by reference in their entirety.

STATEMENT REGARDING FEDERALLY SPONSORED RESEARCH OR DEVELOPMENT

This invention was made with Government support under R01 DE016516 awarded by National Institutes of Health. The Government has certain rights in the invention.

FIELD OF THE INVENTION

The invention is generally related to the field of fabrication and use of biomedical devices, including structural, therapeutic-containing, and cell-encapsulating devices. More specifically, some aspects of the invention relate to improved physical parameters to ensure improved biocompatibility of implanted biomedical devices, including biocompatible hydrogel encapsulating mammalian cells and polymeric particles loaded with anti-inflammatory drugs.

BACKGROUND OF THE INVENTION

Biomaterials and devices transplanted in the body are being used for a broad spectrum of clinical applications such as cell transplantation, controlled drug release, continuous sensing and monitoring of physiological conditions, electronic pacing, and tissue regeneration. For these applications, the longevity and fidelity of the device is highly dependent on its ability to ward off recognition by the host immune system. Immune recognition initiates a cascade of host orchestrated cellular processes leading to foreign body reactions, which include persistent inflammation, fibrosis (walling-off), and damage to the surrounding tissue. These unwanted effects are both deleterious to the function of the device and a significant cause of pain and discomfort for the patient.

In 1980, Lim and Sun, Science 210:908 (1980) introduced an alginate microcapsule coated with an alginate/polylysine complex for encapsulation of pancreatic islets. Hydrogel microcapsules have since been extensively investigated for encapsulation of living cells or cell aggregates for tissue engineering and regenerative medicine (Orive et al., Nat. Medicine 9:104 (2003); Paul, et al., Regen. Med. 4:733 (2009); Read et al., Biotechnol. 19:29 (2001)). In general, capsules are designed to allow facile diffusion of oxygen and nutrients to the encapsulated cells, while releasing the therapeutic proteins secreted by the cells, and to protect the cells from attack by the immune system. These have been developed as potential therapeutics for a range of diseases including type I diabetes, cancer, and neurodegenerative disorders such as Parkinson's (Wilson et al., Adv. Drug. Deliv. Rev. 60:124 (2008); Joki et al., Nat. Biotech. 19:35 (2001); Kishima et al., Neurobiol. Dis. 16:428 (2004)). One of the most common capsule formulations is based on alginate hydrogels, which can be formed through ionic crosslinking. In a typical process, the cells are first blended with a viscous alginate solution. The cell suspension is then processed into micro-droplets using different methods such as air shear, acoustic vibration or electrostatic droplet formation (Rabanel et al., Biotechnol. Prog. 25:946 (2009)). The alginate droplet is gelled upon contact with a solution of divalent ions, such as $Ca^{2+}$ or $Ba^{2+}$.

One challenge associated with alginate microcapsules for cell encapsulation, however, is the lack of control of the relative positions of the cells within the capsules. The cells can become trapped and exposed on the capsule surface, leading to inadequate immune-protection (Wong et al., Biomat. Artific. Cells Immobiol. Biotechnol. 19:675 (1991)). It has been recognized that incomplete coverage would not only cause the rejection of exposed cells but may also allow the infiltration of macrophages and fibroblasts into the capsules through the exposed areas (Chang, Nat, Rev. Drug Discovery 4:221 (2005)). Alginate hydrogel microcapsules have been broadly investigated for their utility with pancreatic islets to treat Type I diabetes (Calafiore, Expert Opin. Biol. Ther. 3:201 (2003)). Numerous promising results have been reported in several animal models including rodents (Lim, Science 210:908 (1980); Qi et al., Artifi. Cells, Blood Substitutes, Biotechnol. 36:403 (2008)), dogs (Soon-Shiong et al., Proc. Natl. Acad. Sci. USA 90:5843 (1993)), and nonhuman primates (El, X. Ma, D. Zhou, I. Vacek, A. M. Sun. J. Clin. Invest. 98:417 (1996)). Clinical trials have also been performed by Soon-Shiong et al., Lancet 343:950 (1994); Elliott et al., Xenotransplantation 14:157 (2007); Calafiore et al., Diabetes Care 29:137 (2006), Basta et al., Diabetes Care 34:2406 (2011); and Tuch et al., Diabetes Care 32:1887 (2009). In general, these clinical trials have reported insulin secretion, but without long term correction of blood sugar control, and additional challenges remain to advance these systems (Tam et al., J. Biomed. Mater. Res. Part A 98A:40 (2011); deVos et al., Biomaterials 27:5603 (2006)).

One challenge is the biocompatibility of the capsules. Upon transplantation, the foreign body responses cause fibrotic cellular overgrowth on the capsules that cut off the diffusion of oxygen and nutrients, and lead to necrosis of encapsulated islets. To this end, research groups have developed polymers to reduce the fibrotic reactions. (Ma et al., Adv. Mater. 23:H189 (2011)). Another challenge is the incomplete coverage of the islets within the capsules (deVos et al., Transplantation 62:888 (1996); deVos et al., Transplantation 62:893 (1996)). Islets protruding outside the capsules are more frequently observed when the islet number density in alginate solution increases or the capsule size decreases, both of which are desirable to minimize the transplantation volume (Leung, et al, Biochem. Eng. J. 48:337 (2010)). It has been hypothesized that if even a small fragment of islet is exposed, immune effector cells may destroy the entire islet (King et al., Graft 4:491 (2001); Weber et al., Ann. NY Acad. Sci. 875:233 (1999)). Furthermore, exposure of a small number of islets may start a cascade of events that leads to enhanced antigen-specific cellular immunity and transplant failure.

A double-encapsulation process (Elliot, 2007; Wong et al., Biomat. Artific. Cells Immobiol. Biotechnol. 19:687 (1991)) has been used to improve the encapsulation and xenograft survival where very small capsules containing cells were first formed and then several small capsules were enclosed in each larger capsule. This approach required two process steps and the large size of the final capsules inevitably limited the mass transport that was essential to cell viability and functionality. As reported by Schneider et al. (Biomaterials 22(14):1961-1970 (2001)), islet containing alginate beads were coated with alternating layers of polyethyleneimine, polyacrylacid or carboxymethylcellulose and alginate to address some of these problems. Thin conformal coating of islets reduces the diffusion distance and total transplantation volume (Teramura et al., Adv. Drug Deliv. Rev. 62:827 (2010); Wilson et al., J. Am. Chem. Soc. 131:18228 (2009)). However, the process often involves multiple steps which cause damage to islets and it is not clear whether the coatings are sufficiently robust for clinical use (Califiore, 2003; Basta et al., Curr. Diab. Rep. 11:384 (2011)). Previous data by Basta et al. (Transpl. Immunol. 13:289 (2004)) has suggested conformal coatings may have reduced immune-protective capacity compared with the hydrogel capsules.

In summary, despite promising studies in various animal models over many years, encapsulated human islets so far have not made an impact in the clinical setting. Many non-immunological and immunological factors such as biocompatibility, reduced immunoprotection, hypoxia, pericapsular fibrotic overgrowth, effects of the encapsulation process, and post-transplant inflammation hamper the successful application of this promising technology (Vaithilinga et al., Diabet Stud 8(1):51-67 (2011)). Currently used alginate microcapsules often have islets protruding outside capsules, leading to inadequate immunoprotection. Improved encapsulation using a two-fluid co-axial electrojetting method to confine islets in the core region of the capsules has been reported by Ma et al., Adv. Healthcare Materials 2(5):667-672 (2013).

One major challenge to clinical application of encapsulated cells and other biomaterials and medical devices is their potential to induce a non-specific host response (Williams, Biomaterials 29(20):2941-53 (2008); Park et al., Pharm Res 13(12):1770-6 (1996); Kvist et al., Diabetes Technol 8(4):463-75 (2006); Wisniewski et al., J Anal Chem 366(6):611-21 (2000); Van der Giessen et al., Circulation 94(7):1690-7 (1996); Granchi et al., J Biomed Mater Res 29(2):197-202 (1995); Ward et al., Obstet Gynecol 86(5):848-50 (1995); Remes et al., Biomaterials 13(11):731-43 (1992)). This reaction involves the recruitment of early innate immune cells such as neutrophils and macrophages, followed by fibroblasts which deposit collagen to form a fibrous capsule surrounding the implanted object (Williams, Biomaterials 29(20):2941-53 (2008); Remes et al., Biomaterials 13(11):731-43 (1992); Anderson et al., Semin Immunol 20(2):86-100 (2008); Anderson et al., Adv Drug Deliver Rev 28(1):5-24 (1997); Abbas et al., Pathologic Basis of Disease. 7th ed. Philadelphia : W.B Saunders (2009)). Fibrotic cell layers can hinder electrical (Singarayar et al., PACE 28(4):311-5 (2005)) or chemical communications and prevent transport of analytes (Sharkawy et al., J Biomed Mater Res 37(3):401-12 (1997); Sharkawy et al., J Biomed Mater Res 40(4):598-605 (1998); Sharkawy et al., J Biomed Mater Res 40(4):586-97 (1998)) and nutrients, thus leading to the eventual failure of many implantable medical devices such as immunoisolated pancreatic islets (De Groot et al., J Surg Res 121(1):141-50 (2004); De Vos et al., Diabetologia 40(3):262-70 (1997); Van Schilfgaarde et al., J Mol Med 77(1):199-205 (1999)).

The fibrotic reactions to the capsules upon transplantation pose a major challenge to transplanting islets. The fibrosis eventually leads to necrosis of islets and failure of transplant.

There remains a substantial need for improved encapsulation methods and devices for transplantation of human islet cells.

It is an object of the present invention to provide a cell encapsulation system for transplanting cells with reduced pericapsular fibrotic overgrowth.

It is a further object of the invention to provide a method for transplanting cells with reduced pericapsular fibrotic overgrowth.

It is a further object of the invention to provide improved methods for treating diabetes using encapsulated islet cells.

It is a further object of the invention to provide a method and devices for general device fabrication to prevent fibrotic sequestration and prevention of function and long-term therapeutic efficacy.

SUMMARY OF THE INVENTION

It has been discovered that biomedical devices designed with certain physical characteristics exhibit reduced host rejection and fibrotic overgrowth of biomaterials and biomedical devices.

A biomedical device for implantation with decreased pericapsular fibrotic overgrowth has been developed. The device includes biocompatible materials, has a diameter of at least 1 mm and less than 10 mm, has a spheroid-like shape, and has one or more of the additional characteristics: surface pores of the device are greater than 0 nm and less than 10 μm; the surface of the device is neutral or hydrophilic; the curvature of the surface of the device is at least 0.2 and is not greater than 2 on all points of the surface; and the surface of the device does not have flat sides, sharp angles, grooves, or ridges. The device elicits less of a fibrotic reaction after implantation than the same device lacking one or more of these characteristic that are present on the device. In some embodiments, the devices can be a biocompatible sphere-like (spheroid) outer shell, encapsulating, for example, biologic cells or tissue, synthetic electrical leads, or sensors.

The biomedical device can be made from a variety of materials, including hydrogels, both chemically purified as well as endotoxin-containing food-grade alginate, semiconducting materials, such as silicon-dioxide-based ceramics like glass, and degradable and non-degradable polymers and plastics, such as PCL and polystyrene. The specific combinations of features result in or improve biocompatibility of devices (in particular, by reducing or eliminating immune reaction to and capsular fibrosis of the devices).

The biomedical device can be used for any biomedical application, including, for example, long-term implantable sensors and actuators, controlled drug releasing devices, prostheses and tissue regenerating biomaterials, and technologies pertaining to transplantation.

A biocompatible capsule encapsulating mammalian cells, optionally including anti-inflammatory drugs, for transplantation with decreased pericapsular fibrotic overgrowth has been developed. The capsule has encapsulated therein mammalian cells. The mammalian cells are not located in the core of the capsule. Preferably the capsule contains two or three layers. In tri-layer capsules, having an acellular core, a hydrogel layer, and an outer barrier layer, the cells are located in the middle layer. For two layer capsules, which contain a core and a shell, the cells are located in the shell. Alternatively, the cells can be in the core of a two layer capsule. Optionally, the capsule also contains one or more therapeutic, diagnostic and/or prophylactic agents, such as anti-inflammatory drugs or radiopaque imaging agents, encapsulated therein.

Generally, the core-shell capsules are fabricated without a membrane layer using a microfluidic or needle system to form capsules and microcapsules with two or more integrated layers. For example, two concurrent liquid streams may be used to form two-layer droplets. The tri-layer capsules can be fabricated without a membrane layer. For example, three concurrent streams may be used to form three-layer droplets that harden to form the capsules and microcapsules.

Cells suitable for encapsulation and transplantation are generally secretory or metabolic cells (i.e., they secrete a therapeutic factor or metabolize toxins, or both) or structural cells (e.g., skin, muscle, blood vessel), or metabolic cells (i.e., they metabolize toxic substances). In some embodiments, the cells are naturally secretory, such as islet cells that naturally secrete insulin, or naturally metabolic, such as hepatocytes that naturally detoxify and secrete. In some embodiments, the cells are bioengineered to express a recombinant protein, such as a secreted protein or metabolic enzyme. Depending on the cell type, the cells may be organized as single cells, cell aggregates, spheroids, or even natural or bioengineered tissue.

The capsule is preferably a hydrogel capsule. In some embodiments the core of the capsule is a non-hydrogel polymer. Preferably the capsules have a diameter greater than 1 mm, more preferably the diameter is 1.5 mm or greater in size, but less than 8 mm. The larger capsules require an acellular core to ensure that the cells are able to receive adequate nutrients and gas exchange by diffusion throughout the hydrogel.

A population of hydrogel capsules encapsulating cells has been developed. Capsules in the population contain cells to be transplanted selected from the group consisting of mammalian secretory cells, mammalian metabolic cells, mammalian structural cells, and aggregates thereof. All of the capsules in the population of capsules have a diameter of at least 1 mm and less than 8 mm. The capsules in the population elicit less of a fibrotic reaction after implantation than the same capsules having a diameter of less than 1 mm. The capsules in the population can be selected by separating capsules having a diameter of at least 1 mm and less than 8 mm from capsules having a diameter of less than 1 mm and from capsules having a diameter of at least 8 mm.

The compositions may be fabricated into artificial organs, such as an artificial pancreas containing encapsulated islet cells. In some of these embodiments, the cells are encapsulated in a single hydrogel compartment. In other embodiments, the composition contains a plurality of encapsulated cells dispersed or encapsulated in a biocompatible structure.

Methods for treating diseases generally involve administering to a subject a biocompatible hydrogel encapsulating mammalian cells and anti-inflammatory drugs. In some embodiments, the anti-inflammatory drugs are encapsulated in controlled release polymer. In some of these embodiments, the encapsulated cells preferably secrete a therapeutically effective amount of a substance to treat the disease for at least 30 days, preferably at least 60 days, more preferably at least 90 days. In particularly preferred embodiments, the cells are islet cells that secrete a therapeutically effective amount of insulin to treat diabetes in the subject for at least 30 days, preferably at least 60 days, more preferably at least 90 days.

BRIEF DESCRIPTION OF THE DRAWINGS

FIG. 4A shows the blood glucose data of STZ-induced diabetic mice after the transplantation of 500 encapsulated rat islet equivalents. The error bars represent standard errors. FIG. 4B shows the number of normoglycemic mice as a function of time. 8 replicates were used for both types of capsules.

FIG. 9A), Ly6g (neutrophil marker; FIG. 9B), CD11b (myeloid cell marker; FIG. 9C), and Col1a1 (fibrosis marker; FIG. 9D).

DETAILED DESCRIPTION OF THE INVENTION

I. Definitions

Figure 1:
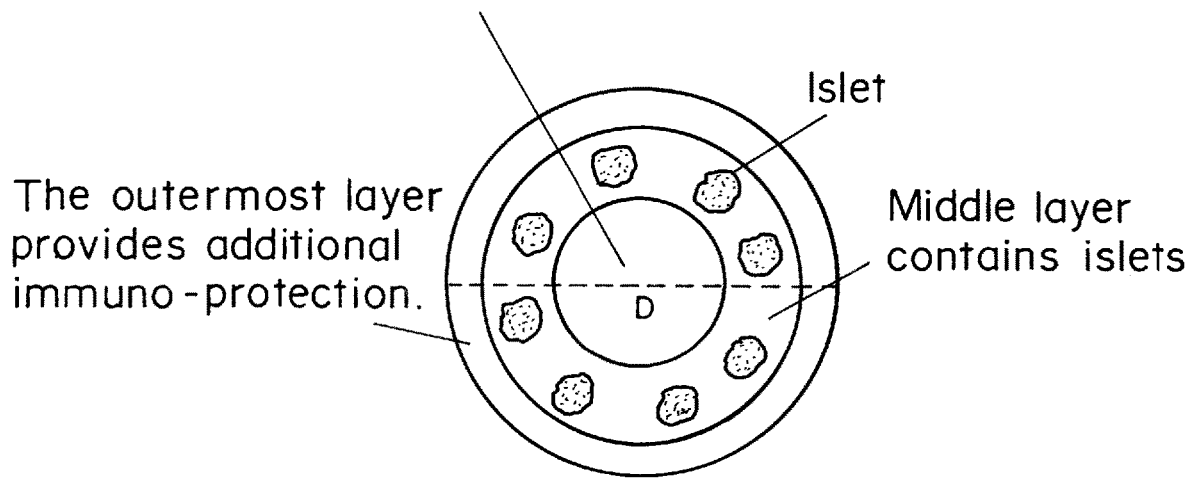
FIG. 1 is an illustration of a tri-layer capsule, with the cells encapsulated in a core hydrogel and the drug-loaded particles contained in an outer (envelope) hydrogel. An optional membrane material is shown separating the core and envelope hydrogels.

"Hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer that forms a gel which is not toxic to living cells, and allows sufficient diffusion of oxygen and nutrients to the entrapped cells to maintain viability.

"Alginate" is a collective term used to refer to linear polysaccharides formed from β-D-mannuronate and α-L-guluronate in any M/G ratio, as well as salts and derivatives thereof. The term "alginate", as used herein, encompasses any polymer having the structure shown below, as well as salts thereof.

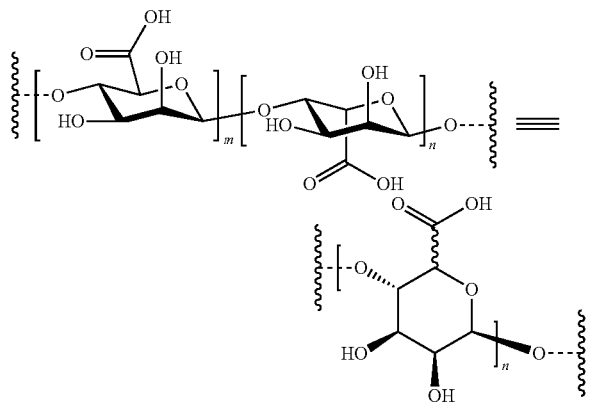

"Biocompatible" generally refers to a material and any metabolites or degradation products thereof that are generally non-toxic to the recipient and do not cause any significant adverse effects to the subject.

"Biodegradable" generally refers to a material that will degrade or erode by hydrolysis or enzymatic action under physiologic conditions to smaller units or chemical species that are capable of being metabolized, eliminated, or excreted by the subject. The degradation time is a function of polymer composition and morphology.

"Drug-loaded particle" refers to a polymeric particle having a drug dissolved, dispersed, entrapped, encapsulated, or attached thereto.

"Microparticle" and "nanoparticle" refer to a polymeric particle of microscopic and nanoscopic size, respectively, optionally containing a drug dissolved, dispersed, entrapped, encapsulated, or attached thereto.

"Anti-inflammatory drug" refers to a drug that directly or indirectly reduces inflammation in a tissue. The term includes, but is not limited to, drugs that are immunosuppressive. The term includes anti-proliferative immunosuppressive drugs, such as drugs that inhibit the proliferation of lymphocytes.

"Immunosuppressive drug" refers to a drug that inhibits or prevents an immune response to a foreign material in a subject Immunosuppressive drugs generally act by inhibiting T-cell activation, disrupting proliferation, or suppressing inflammation. A person who is undergoing immunosuppression is said to be immunocompromised.

"Mammalian cell" refers to any cell derived from a mammalian subject suitable for transplantation into the same or a different subject. The cell may be xenogeneic, autologous, or allogeneic. The cell can be a primary cell obtained directly from a mammalian subject. The cell may also be a cell derived from the culture and expansion of a cell obtained from a subject. For example, the cell may be a stem cell Immortalized cells are also included within this definition. In some embodiments, the cell has been genetically engineered to express a recombinant protein and/or nucleic acid.

"Autologous" refers to a transplanted biological substance taken from the same individual.

"Allogeneic" refers to a transplanted biological substance taken from a different individual of the same species.

"Xenogeneic" refers to a transplanted biological substance taken from a different species.

"Islet cell" refers to an endocrine cell derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogenous populations of these cells. In preferred embodiments, a population of islet cells contains at least beta cells.

"Transplant" refers to the transfer of a cell, tissue, or organ to a subject from another source. The term is not limited to a particular mode of transfer. Encapsulated cells may be transplanted by any suitable method, such as by injection or surgical implantation.

"Spheroid-like shape" refers to an object having a surface that roughly forms a spheroid. Beyond a perfect or classical sphere, oblate spheroid, or prolate spheroid shape, a spheroid-like shape can have waves and undulations. Generally, a spheroid-like shape is an ellipsoid (for its averaged surface) with semi-principal axes within 100% of each other. The diameter of a spheroid-like shape is the average diameter, such as the average of the semi-principal axes.

"Flat side" refers to a contiguous area of more than 5% of a surface that has a curvature of 0.

"Sharp angle" refers to a location on a surface across which the tangent to the surface changes by more than 10% over a distance of 2% or less of the circumference of the surface. Edges, corners, grooves, and ridges in a surface are all forms of sharp angles.

II. Biomedical Devices and Capsules

A. Biomedical Devices with Reduced Fibrosis

Biomedical devices are disclosed for implantation into a subject. The devices are formed from biocompatible materials, such as biocompatible polymers, biodegradable and non-biodegradable polymers, semiconductor materials, ceramics, and glass. In order to reduce or prevent fibrosis, the devices should include some or all of a suite of characteristics:

(1) Size: The device should have a minimum diameter of 1 mm (preferable 1.5 mm). The diameter can be increased upwards of 8 to 10 mm.

(2) Shape: The overall device should be a sphere, sphere-like, spheroid, or spheroid-like. The curvature at any point on the surface of the device should be no less than 0.2 and no more than 2. Surface pores are ignored for the purpose of calculating the curvature of the surface of the device.

(3) Hydrophobicity: The surface of the device should either be neutral or more water-loving (hydrophilic), and should not have a hydrophobic chemistry, such as with Teflon.

(4) Surface pore size: Pores on the surface of the device should be above 0 nm but should not exceed 10 μm.

(5) Surface topography: The device should not have any flat sides, sharp angles, grooves, or ridges.

These characteristics have been discovered to affect the fibrosis of implanted devices. Devices having the first two characteristics and at least one of the other characteristics have been shown to exhibit reduced fibrosis. Devices can be made with any one or combination of these characteristics. Devices having all of these characteristics are preferred. Generally, the disclosed devices will elicit less of a fibrotic reaction after implantation than the same device having any one or more of these characteristics. In some embodiments, the device will elicit less of a fibrotic reaction after implantation than the same device having the first two characteristics and at least one of the other characteristics. In some embodiments, the device will elicit less of a fibrotic reaction after implantation than the same device having all of the characteristics. In some embodiments, the biomedical devices are capsules or hydrogel capsules as described herein. Reference herein to a capsule or a hydrogel capsule is intended to also refer to a biomedical device of the same description as the referenced capsule.

The disclosed devices have advantages and improvements over existing devices and materials. For example, it has been discovered that objects with flat surfaces (curvature of zero), such as cylinders, become fibrosed even if they are large in overall size (over 1 mm). On the other extreme, objects with a high curvature (and thus having too small a diameter, i.e., less than 1 mm), are capable of high packing densities with other transplanted materials and/or surrounding tissue, which facilitates immune cell adherence and fibrotic deposition. It has been established that the specific combination of features together reduce or prevent fibrosis of many material classes, including hydrogels (both chemically purified as well as endotoxin-containing food-grade alginate), semiconducting materials (such as silicon-dioxide-based ceramics like glass), and degradable and non-degradable polymers and plastics (such as PCL and polystyrene). Thus, the disclosed devices can be made of these and a wide variety of other materials.

Hydrogel alginate spheres with the identified characteristics have been generated and demonstrated to prevent fibrosis and ensure long-term viability and functionality of transplanted mammalian cells of various origin (i.e., rat, mouse, pig, human) for treatment of disease (type 1 diabetes). Optionally, the shell of the device may also contain one or more therapeutic agents (such as anti-inflammatories) or diagnostic agents (such as oxygen sensing or imaging chemistries).

The biomedical device can be used for any biomedical application, including, for example, long-term implantable sensors and actuators, controlled drug releasing devices, prostheses and tissue regenerating biomaterials, and technologies pertaining to implantation and transplantation. Many biomedical devices and purposes are known and the disclosed devices can be adapted for such purposes.

B. Encapsulated Cells with Reduced Fibrosis

Capsules are disclosed for transplanting mammalian cells into a subject. The capsules are formed from a biocompatible, hydrogel-forming polymer encapsulating the cells to be transplanted. In order to inhibit capsular overgrowth (fibrosis), the structure of the capsules prevents cellular material from being located on the surface of the capsule. Additionally, the structure of the capsules ensures that adequate gas exchange occurs with the cells and nutrients are received by the cells encapsulated therein. Optionally, the capsules also contain one or more anti-inflammatory drugs encapsulated therein for controlled release.

C. Biocompatible Polymers

The disclosed compositions are formed from a biocompatible, hydrogel-forming polymer encapsulating the cells to be transplanted. Examples of materials which can be used to form a suitable hydrogel include polysaccharides such as alginate, collagen, chitosan, sodium cellulose sulfate, gelatin and agarose, water soluble polyacrylates, polyphosphazines, poly(acrylic acids), poly(methacrylic acids), poly(alkylene oxides), poly(vinyl acetate), polyvinylpyrrolidone (PVP), and copolymers and blends of each. See, for example, U.S. Pat. Nos. 5,709,854, 6,129,761 and 6,858,229.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups and sulfonic acid groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

The biocompatible, hydrogel-forming polymer is preferably a water-soluble gelling agent. In preferred embodiments, the water-soluble gelling agent is a polysaccharide gum, more preferably a polyanionic polymer.

The cells are preferably encapsulated using an anionic polymer such as alginate to provide the hydrogel layer (e.g., core), where the hydrogel layer is subsequently cross-linked with a polycationic polymer (e.g., an amino acid polymer such as polylysine) to form a shell. See e.g., U.S. Pat. Nos. 4,806,355, 4,689,293 and 4,673,566 to Goosen et al.; U.S. Pat. Nos. 4,409,331, 4,407,957, 4,391,909 and 4,352,883 to Lim et al.; U.S. Pat. Nos. 4,749,620 and 4,744,933 to Rha et al.; and U.S. Pat. No. 5,427,935 to Wang et al, Amino acid polymers that may be used to crosslink hydrogel forming polymers such as alginate include the cationic poly(amino acids) such as polylysine, polyarginine, polyornithine, and copolymers and blends thereof 1. Polysaccharides Several mammalian and non-mammalian polysaccharides have been explored for cell encapsulation. Exemplary polysaccharides suitable for cell encapsulation include alginate, chitosan, hyaluronan (HA), and chondroitin sulfate. Alginate and chitosan form crosslinked hydrogels under certain solution conditions, while HA and chondroitin sulfate are preferably modified to contain crosslinkable groups to form a hydrogel.

In preferred embodiments, the biocompatible, hydrogel-forming polymer encapsulating the cells is an alginate. Alginates are a family of unbranched anionic polysaccharides derived primarily from brown algae which occur extracellularly and intracellularly at approximately 20% to 40% of the dry weight. The 1,4-linked α-1-guluronate (G) and β-d-mannuronate (M) are arranged in homopolymeric (GGG blocks and MMM blocks) or heteropolymeric block structures (MGM blocks). Cell walls of brown algae also contain 5% to 20% of fucoidan, a branched polysaccharide sulphate ester with 1-fucose four-sulfate blocks as the major component. Commercial alginates are often extracted from algae washed ashore, and their properties depend on the harvesting and extraction processes.

Alginate forms a gel in the presence of divalent cations via ionic crosslinking. Although the properties of the hydrogel can be controlled to some degree through changes in the alginate precursor (molecular weight, composition, and macromer concentration), alginate does not degrade, but rather dissolves when the divalent cations are replaced by monovalent ions. In addition, alginate does not promote cell interactions.

A particularly preferred composition is a capsule or microcapsule containing cells immobilized in a core of alginate with a polylysine shell. Preferred capsules and microcapsules may also contain an additional external alginate layer (e.g., envelope) to form a multi-layer alginate/polylysine-alginate/alginate-cells capsule or microcapsule. See U.S. Pat. No. 4,391,909 to Lim et al., for description of alginate hydrogel crosslinked with polylysine. Other cationic polymers suitable for use as a cross-linker in place of polylysine include poly(β-amino alcohols) (PBAAs) (Ma M et al., Adv. Mater. 23:H189-94 (2011).

Chitosan is made by partially deacetylating chitin, a natural nonmammalian polysaccharide, which exhibits a close resemblance to mammalian polysaccharides, making it attractive for cell encapsulation. Chitosan degrades predominantly by lysozyme through hydrolysis of the acetylated residues. Higher degrees of deacetylation lead to slower degradation times, but better cell adhesion due to increased hydrophobicity. Under dilute acid conditions (pH<6), chitosan is positively charged and water soluble, while at physiological pH, chitosan is neutral and hydrophobic, leading to the formation of a solid physically crosslinked hydrogel. The addition of polyol salts enables encapsulation of cells at neutral pH, where gelation becomes temperature dependent.

Chitosan has many amine and hydroxyl groups that can be modified. For example, chitosan has been modified by grafting methacrylic acid to create a crosslinkable macromer while also grafting lactic acid to enhance its water solubility at physiological pH. This crosslinked chitosan hydrogel degrades in the presence of lysozyme and chondrocytes. Photopolymerizable chitosan macromer can be synthesized by modifying chitosan with photoreactive azidobenzoic acid groups. Upon exposure to UV in the absence of any initiator, reactive nitrene groups are formed that react with each other or other amine groups on the chitosan to form an azo crosslink.

Hyaluronan (HA) is a glycosaminoglycan present in many tissues throughout the body that plays an important role in embryonic development, wound healing, and angiogenesis. In addition, HA interacts with cells through cell-surface receptors to influence intracellular signaling pathways. Together, these qualities make HA attractive for tissue engineering scaffolds. HA can be modified with crosslinkable moieties, such as methacrylates and thiols, for cell encapsulation. Crosslinked HA gels remain susceptible to degradation by hyaluronidase, which breaks HA into oligosaccharide fragments of varying molecular weights. Cells can be encapsulated in photopolymerized HA hydrogels where the gel structure is controlled by the macromer concentration and macromer molecular weight. In addition, photopolymerized HA and dextran hydrogels maintain long-term culture of undifferentiated human embryonic stem cells. HA hydrogels have also been fabricated through Michael-type addition reaction mechanisms where either acrylated HA is reacted with PEG-tetrathiol, or thiol-modified HA is reacted with PEG diacrylate.

Chondroitin sulfate makes up a large percentage of structural proteoglycans found in many tissues, including skin, cartilage, tendons, and heart valves, making it an attractive biopolymer for a range of tissue engineering applications. Photocrosslinked chondroitin sulfate hydrogels can be been prepared by modifying chondroitin sulfate with methacrylate groups. The hydrogel properties were readily controlled by the degree of methacrylate substitution and macromer concentration in solution prior to polymerization. Further, the negatively charged polymer creates increased swelling pressures allowing the gel to imbibe more water without sacrificing its mechanical properties. Copolymer hydrogels of chondroitin sulfate and an inert polymer, such as PEG or PVA, may also be used.

2. Synthetic Polymers

Polyethylene glycol (PEG) has been the most widely used synthetic polymer to create macromers for cell encapsulation. A number of studies have used poly(ethylene glycol) di(meth)acrylate to encapsulate a variety of cells. Biodegradable PEG hydrogels can be been prepared from triblock copolymers of poly(α-hydroxy esters)-b-poly (ethylene glycol)-b-poly(α-hydroxy esters) endcapped with (meth)acrylate functional groups to enable crosslinking. PLA and poly(8-caprolactone) (PCL) have been the most commonly used poly(a-hydroxy esters) in creating biodegradable PEG macromers for cell encapsulation. The degradation profile and rate are controlled through the length of the degradable block and the chemistry. The ester bonds may also degrade by esterases present in serum, which accelerates degradation. Biodegradable PEG hydrogels can also be fabricated from precursors of PEG-bis-[2-acryloyloxy propanoate]. As an alternative to linear PEG macromers, PEG-based dendrimers of poly(glycerol-succinic acid)-PEG, which contain multiple reactive vinyl groups per PEG molecule, can be used. An attractive feature of these materials is the ability to control the degree of branching, which consequently affects the overall structural properties of the hydrogel and its degradation. Degradation will occur through the ester linkages present in the dendrimer backbone.

The biocompatible, hydrogel-forming polymer can contain polyphosphoesters or polyphosphates where the phosphoester linkage is susceptible to hydrolytic degradation resulting in the release of phosphate. For example, a phosphoester can be incorporated into the backbone of a crosslinkable PEG macromer, poly(ethylene glycol)-di-[ethylphosphatidyl (ethylene glycol) methacrylate] (PhosPEG-dMA), to form a biodegradable hydrogel. The addition of alkaline phosphatase, an ECM component synthesized by bone cells, enhances degradation. The degradation product, phosphoric acid, reacts with calcium ions in the medium to produce insoluble calcium phosphate inducing autocalcification within the hydrogel. Poly(6-aminoethyl propylene phosphate), a polyphosphoester, can be modified with methacrylates to create multivinyl macromers where the degradation rate was controlled by the degree of derivitization of the polyphosphoester polymer.

Polyphosphazenes are polymers with backbones consisting of nitrogen and phosphorous separated by alternating single and double bonds. Each phosphorous atom is covalently bonded to two side chains. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom.

D. Conjugation of Drugs to Hydrogel-Forming Polymer

In some embodiments, one or more anti-inflammatory drugs are covalently attached to the hydrogel forming polymer. In these cases, the anti-inflammatory drugs are attached to the hydrogel forming polymer via a linking moiety that is designed to be cleaved in vivo. The linking moiety can be designed to be cleaved hydrolytically, enzymatically, or combinations thereof, so as to provide for the sustained release of the anti-inflammatory drug in vivo. Both the composition of the linking moiety and its point of attachment to the anti-inflammatory agent, are selected so that cleavage of the linking moiety releases either an anti-inflammatory agent, or a suitable prodrug thereof. The composition of the linking moiety can also be selected in view of the desired release rate of the anti-inflammatory agents.

Linking moieties generally include one or more organic functional groups. Examples of suitable organic functional groups include secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, —NRCONR—), carbinols (—CHOH—, —CROH—), disulfide groups, hydrazones, hydrazides, ethers (—O—), and esters (—COO—, —CH$_2$O$_2$C—, CHRO$_2$C—), wherein R is an alkyl group, an aryl group, or a heterocyclic group. In general, the identity of the one or more organic functional groups within the linking moiety can be chosen in view of the desired release rate of the anti-inflammatory agents. In addition, the one or more organic functional groups can be chosen to facilitate the covalent attachment of the anti-inflammatory agents to the hydrogel forming polymer. In preferred embodiments, the linking moiety contains one or more ester linkages which can be cleaved by simple hydrolysis in vivo to release the anti-inflammatory agents.

In certain embodiments, the linking moiety includes one or more of the organic functional groups described above in combination with a spacer group. The spacer group can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, most preferably between 3 and 50 atoms. Examples of suitable spacer groups include alkyl groups, heteroalkyl groups, alkylaryl groups, oligo- and polyethylene glycol chains, and oligo- and poly(amino acid) chains. Variation of the spacer group provides additional control over the release of the anti-inflammatory agents in vivo. In embodiments where the linking moiety includes a spacer group, one or more organic functional groups will generally be used to connect the spacer group to both the anti-inflammatory agent and the hydrogel forming polymer.

In certain embodiments, the one or more anti-inflammatory agents are covalently attached to the hydrogel forming polymer via a linking moiety which contains an alkyl group, an ester group, and a hydrazide group. By way of example, conjugation of the anti-inflammatory agent dexamethasone to alginate can be via a linking moiety containing an alkyl group, an ester group connecting the alkyl group to the anti-inflammatory agent, and a hydrazide group connecting the alkyl group to carboxylic acid groups located on the alginate. In this embodiment, hydrolysis of the ester group in vivo releases dexamethasone at a low dose over an extended period of time.

Reactions and strategies useful for the covalent attachment of anti-inflammatory agents to hydrogel forming polymers are known in the art. See, for example, March, "Advanced Organic Chemistry," 5$^{th}$ Edition, 2001, Wiley-Interscience Publication, New York) and Hermanson, "Bioconjugate Techniques," 1996, Elsevier Academic Press, U.S.A. Appropriate methods for the covalent attachment of a given anti-inflammatory agent can be selected in view of the linking moiety desired, as well as the structure of the anti-inflammatory agents and hydrogel forming polymers as a whole as it relates to compatibility of functional groups, protecting group strategies, and the presence of labile bonds.

E. Anti-Inflammatory and Anti-Proliferative Drugs

Drugs suitable for use in the disclosed compositions are described and can be identified using disclosed methods. Representative drugs include glucocorticoids, phenolic antioxidants, anti-proliferative drugs, or combinations thereof. These are collectively referred to herein as "anti-inflammatory drugs" unless stated otherwise.

Non-limiting examples include steroidal anti-inflammatories. Particularly preferred steroidal anti-inflammatory drugs include dexamethasone, 5-FU, daunomycin, and mitomycin. Anti-angiogenic or anti-proliferative drugs are also useful. Examples include curcumins including monoesters and tetrahydrocurcumin, and drugs such as sirolimus (rapamycin), ciclosporin, tacrolimus, doxorubicin, mycophenolic acid and paclitaxel and derivatives thereof. In some embodiments, the anti-inflammatory drug is an mTOR inhibitor (e.g., sirolimus and everolimus). A new antiproliferative drug is biolimus A9, a highly lipophilic, semisynthetic sirolimus analogue with an alkoxy-alkyl group replacing hydrogen at position 42-O. Lisofylline is a synthetic small molecule with anti-inflammatory properties. In some embodiments, the anti-inflammatory drug is a calcineurin inhibitor (e.g., cyclosporine, pimecrolimus and tacrolimus).

In some embodiments, the anti-inflammatory drug is a synthetic or natural anti-inflammatory protein. Antibodies specific to select immune components can be added to immunosuppressive therapy. In some embodiments, the anti-inflammatory drug is an anti-T cell antibody (e.g., anti-thymocyte globulin or Anti-lymphocyte globulin), anti-IL-2Rα receptor antibody (e.g., basiliximab or daclizumab), or anti-CD20 antibody (e.g., rituximab).

In preferred embodiments, the one or more anti-inflammatory drugs are released from the capsules after administration to a mammalian subject in an amount effective to inhibit fibrosis of the composition for at least 30 days, preferably at least 60 days, more preferably at least 90 days. In some embodiments, the anti-inflammatory drugs provide spatially localized inhibition of inflammation in the subject without systemic immunosuppression for at least 10 days, preferably at least 14 days, more preferably at least 30 days. In some embodiments, spatially localized inflammation is detected by measuring cathepsin activity at the injection sites in the subject. In other embodiments, spatially localized inflammation is detected by measuring reactive oxygen species (ROS) at the injection site in the subject. In some embodiments, systemic immunosuppression is detected by measuring no cathepsin activity or ROS at control sites in the subject, e.g., sites injected with drug-free polymeric particle or hydrogel. Methods for identifying, selecting, and optimizing anti-inflammatory drugs for use in the disclosed compositions are described below.

The release rate and amounts can be selected in part by modifying drug loading of the polymeric particle. As disclosed herein, higher drug loading can cause a significant initial burst release. This can also result in systemic immunosuppression rather than spatially localized inhibition of inflammation. In contrast, drug loading levels that are too low will not release therapeutically effective amounts of anti-inflammatory drug.

The optimal drug loading will necessarily depend on many factors, including the choice of drug, polymer, hydrogel, cell, and site of implantation. In some embodiments, the one or more anti-inflammatory drugs are loaded in the polymeric particle at a concentration of about 0.01% to about 15%, preferably about 0.1% to about 5%, more preferably about 1% to about 3% by weight. In some embodiments, the one or more anti-inflammatory drugs are encapsulated in the hydrogel at a concentration of 0.01 to 10.0 mg/ml of hydrogel, preferably 0.1 to 4.0 mg/ml of hydrogel, more preferably 0.3 to 2.0 mg/ml of hydrogel. However, optimal drug loading for any given drug, polymer, hydrogel, cell, and site of transplantation can be identified by routine methods, such as those described herein.

F. Biodegradable Polymers for Drug Delivery

The drug-loaded particles containing anti-inflammatory drugs are preferably formed from a biocompatible, biodegradable polymer suitable for drug delivery. In general, synthetic polymers are preferred, although natural polymers may be used and have equivalent or even better properties, especially some of the natural biopolymers which degrade by hydrolysis, such as some of the polyhydroxyalkanoates.

Representative synthetic polymers include poly(hydroxy acids) such as poly(lactic acid), poly(glycolic acid), and poly(lactic acid-co-glycolic acid), poly(lactide), poly(glycolide), poly(lactide-co-glycolide), polyanhydrides, poly-orthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles and microparticles can be adjusted during the production by using polymers such as poly(lactide-co-glycolide) copolymerized with PEG.

In the most preferred embodiment, PLGA is used as the biodegradable polymer. PLGA particles and microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. For example, the hydrophobic poly (lactic acid) (PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

The diameter and porosity of the drug-loaded particle can be optimized based on the drug to be delivered and the desired dosage and rate of release. In preferred embodiments, the drug-loaded particle is a microparticle or a nanoparticle. In more preferred embodiments, the drug-loaded particle is a particle. The mean diameter of the particle may be selected and optimized based on the particular drug, dosage, and release rate needed. In preferred embodiments, the drug loaded polymeric particles are microparticles having a mean diameter of about 1 μm to about 100 μm, preferably about 1 μm to about 50 μm, more preferably about 1 μm to about 10 μm. In other embodiments, drug loaded polymeric particles are nanoparticles having a mean diameter of about 10 nm to about 999 nm, including at least about 50 nm, preferably at least about 100 nm, more preferably at least about 200 nm. In more preferred embodiments, the drug-loaded polymeric particles have a mean diameter that is greater than 1 mm, preferably 1.5 mm or greater. In some embodiments, the drug-loaded polymeric particles can be as large at 8 mm in diameter.

G. Capsules

The capsules are two or three layer capsules. Preferably the capsules have a mean diameter that is greater than 1 mm, preferably 1.5 mm or greater. In some embodiments, the capsules can be as large at 8 mm in diameter. For example, the capsule can be in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, or 1.5 mm to 2 mm.

The rate of molecules entering the capsule necessary for cell viability and the rate of therapeutic products and waste material exiting the capsule membrane are selected by modulating macrocapsule permeability. Macrocapsule permeability is also modified to limit entry of immune cells, antibodies, and cytokines into the capsule or microcapsule.

It has been shown that, since different cell types have different metabolic requirements, the permeability of the membrane has to be optimized based on the cell type encapsulated in the hydrogel. The diameter of the capsules or microcapsules is an important factor that influences both the immune response towards the cell capsules as well as the mass transport across the capsule membrane.

H. Cells

The cell type chosen for encapsulation in the disclosed compositions depends on the desired therapeutic effect. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. Anti-inflammatory drugs combat the immune response elicited by the presence of such cells. In the case of autologous cells, the anti-inflammatory drugs reduce the immune response provoked by the presence of the foreign hydrogel materials or due to the trauma of the transplant surgery. Cells can be obtained from biopsy or excision of the patient or a donor, cell culture, or cadavers.

In some embodiments, the cells secrete a therapeutically effective substance, such as a protein or nucleic acid. In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid.

Examples of cells for encapsulation include hepatocytes, islet cells, parathyroid cells, cells of intestinal origin, cells derived from the kidney, and other cells acting primarily to synthesize and secret, or to metabolize materials. A preferred cell type is a pancreatic islet cell. Genetically engineered cells are also suitable for encapsulation according to the disclosed methods. In some embodiments, the cells are engineered to secrete blood clotting factors, e.g., for hemophilia treatment, or to secrete growth hormones for treatment of individuals who are genetically deficient. Alternatively, the cells may be engineered to produce substances that are targeted to cancers or other deleterious materials. In some embodiments, the cells are contained in natural or bioengineered tissue. In some embodiments, the cells are suitable for transplantation into the central nervous system for treatment of neurodegenerative disease.

The amount and density of cells encapsulated in the disclosed compositions, such as capsules and microcapsules, will vary depending on the choice of cell, hydrogel, and site of implantation. In some embodiments, the single cells are present in the hydrogel at a concentration of $0.1 \times 10^6$ to $4 \times 10^6$ cells/ml, preferably $0.5 \times 10^6$ to $2 \times 10^6$ cells/ml. In other embodiments, the cells are present as cell aggregates. For example, islet cell aggregates (or whole islets) preferably contain about 1500-2000 cells for each aggregate of 150 µm diameter, which is defined as one islet equivalent (IE). Therefore, in some embodiments, islet cells are present at a concentration of 100-10000 IE/ml, preferably 200-3,000 IE/ml, more preferably 500-1500 IE/ml.

1. Islet Cells

In preferred embodiments, the disclosed compositions contain islet cells producing insulin. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al., The isolated pancreatic cells may optionally be cultured prior to encapsulation or microencapsulation, using any suitable method of culturing islet cells as is known in the art. See e.g., U.S. Pat. No. 5,821,121 to Brothers. Isolated cells may be cultured in a medium under conditions that helps to eliminate antigenic components.

2. Genetically Engineered Cells

In some embodiments, the disclosed compositions contain cells genetically engineered to produce a therapeutic protein or nucleic acid. In these embodiments, the cell can be a stem cell (e.g., pluripotent), a progenitor cell (e.g., multipotent or oligopotent), or a terminally differentiated cell (i.e., unipotent). The cell can be engineered to contain a nucleic acid encoding a therapeutic polynucleotide such miRNA or RNAi or a polynucleotide encoding a protein. The nucleic acid can be integrated into the cells genomic DNA for stable expression or can be in an expression vector (e.g., plasmid DNA). The therapeutic polynucleotide or protein can be selected based on the disease to be treated and the site of transplantation. In some embodiments, the therapeutic polynucleotide or protein is anti-neoplastic. In other embodiments, the therapeutic polynucleotide or protein is a hormone, growth factor, or enzyme.

III. Methods of Making Capsule

A. Method for Making Bi and Tri-layer Capsules

Triple layer capsules can be made by a tri-fluid coaxial electrospraying process.

Figure 2:
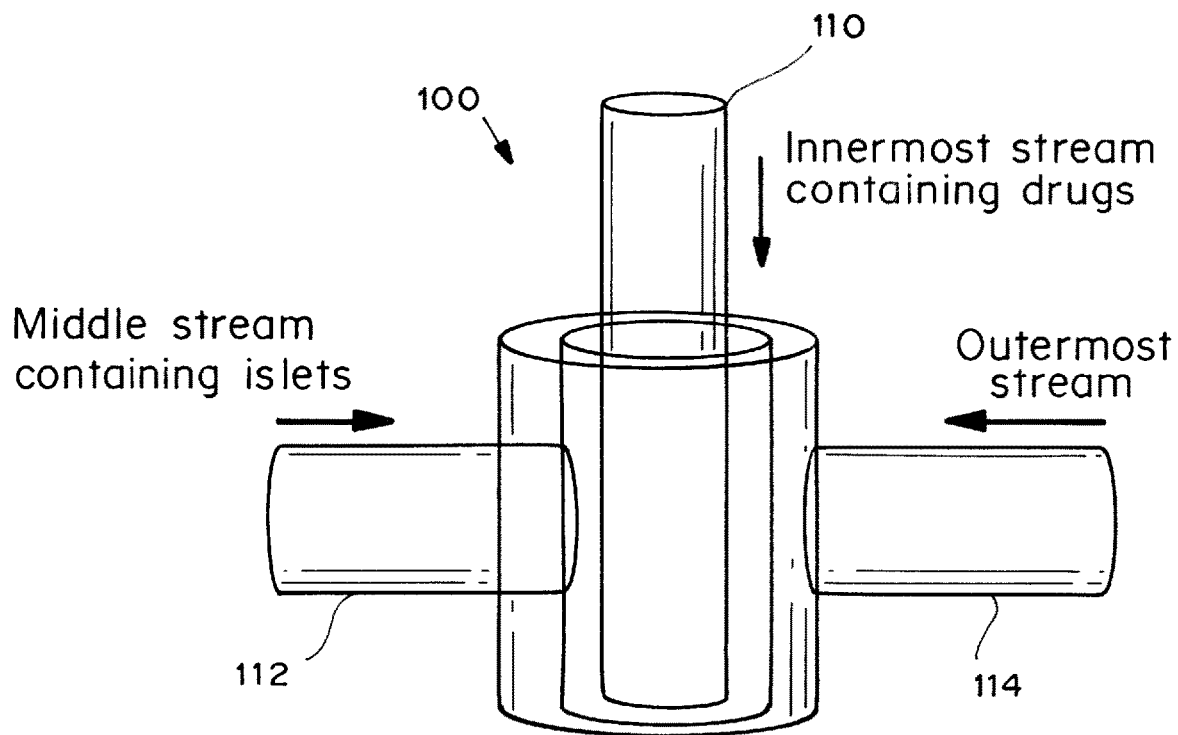
FIG. 2 is an illustration of a nozzle for forming tri-layer capsules via tri-fluid coaxial electrospraying.

Preferably the three layer capsules are formed in an electrospraying device with a nozzle that consists of three separate concentric tubes at its outlet. An exemplary nozzle (100) is illustrated in FIG. 2. A first stream that contains a hydrogel forming material, optionally including one or more anti-inflammatory drugs or imaging reagents, is pumped into the innermost tube (110) of the nozzle. A second stream that contains hydrogel forming material and islets is pumped into the middle tube (112) of the nozzle. A third stream that contains a hydrogel forming material is delivered to the outermost tube (114).

The three streams meet at the outlet of the nozzle. The relatively high viscosity of the alginate solution prevents any significant intermixing among the three streams and droplets with three distinct concentric layers are formed under the electric field. After the droplets fall into the gel bath which contains divalent ions such as Calcium or Barium ions, crosslinking occurs instantaneously and triple-layer capsules are formed. The triple layer capsules can be made by a tri-fluid coaxial electrospraying.

For example, a stream that contains anti-inflammatory drugs or imaging reagents is pumped into the innermost tube; a second stream that contains islets is pumped into the middle tube; and another stream is delivered to the outermost tube. The three streams meet at the outlet of the nozzle. The relatively high viscosity of the alginate solution prevents any significant intermixing among the three streams and droplets with three distinct concentric layers are formed under the electric field. After the droplets fall into the gel bath which contains divalent ions such as Calcium or Barium ions, crosslinking occurs instantaneously and triple-layer capsules are formed.

B. Methods for Making Two Layer Capsules

Two-fluid co-axial electro jetting is used for the fabrication of core-shell capsules and encapsulation of cells or cell aggregates. In the preferred embodiment, the shell fluid consists of a cell-free alginate solution, while the core fluid contains the islets or other therapeutic cells. The relatively high viscosity of the two fluids and short interaction time between them prevent their intermixing. Under electrostatic force, microdroplets with core-shell structures are formed and converted to hydrogel capsules in a gelling bath containing divalent crosslinking ions.

C. Cell Encapsulation with Polysaccharide Hydrogel

Methods for encapsulating cells in hydrogels are known. In preferred embodiments, the hydrogel is a polysaccharide. For example, methods for encapsulating mammalian cells in an alginate polymer are well known and briefly described below. See, for example, U.S. Pat. No. 4,352,883 to Lim.

Alginate can be ionically cross-linked with divalent cations, in water, at room temperature, to form a hydrogel matrix. An aqueous solution containing the biological materials to be encapsulated is suspended in a solution of a water soluble polymer, the suspension is formed into droplets which are configured into discrete capsules or microcapsules by contact with multivalent cations, then the surface of the capsules or microcapsules is crosslinked with polyamino acids to form a semipermeable membrane around the encapsulated materials.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N+-\backslash\!\Lambda\!\backslash/-+NR_3$ can also be used. Aqueous solutions of the salts of these cations are added to the polymers to form soft, highly swollen hydrogels and membranes. The higher the concentration of cation, or the higher the valence, the greater is the degree of cross-linking of the polymer. Concentrations from as low as 0.005 M have been demonstrated to cross-link the polymer. Higher concentrations are limited by the solubility of the salt.

The preferred anions for cross-linking of polymers containing basic side chains to form a hydrogel are divalent and trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

In a preferred embodiment, alginate capsules are fabricated from solution of alginate containing suspended cells using the encapsulator (such as an Inotech encapsulator). In some embodiments, alginates are ionically crosslinked with a polyvalent cation, such as $Ca^{2+}$, $Ba^{2+}$, or $Sr^{2+}$. In particularly preferred embodiments, the alginate is crosslinked using $BaCl_2$. In some embodiments, the capsules are further purified after formation. In preferred embodiments, the capsules are washed with, for example, HEPES solution, Krebs solution, and/or RPMI-1640 medium.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell attachment and viability can be assessed using standard techniques, such as histology and fluorescent microscopy. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space.

When desired, the capsules or microcapsules may be treated or incubated with a physiologically acceptable salt such as sodium sulfate or like agents, in order to increase the durability of the capsules or microcapsule, while retaining or not unduly damaging the physiological responsiveness of the cells contained in the capsules or microcapsules. By "physiologically acceptable salt" is meant a salt that is not unduly deleterious to the physiological responsiveness of the cells encapsulated in the capsules or microcapsules. In general, such salts are salts that have an anion that binds calcium ions sufficiently to stabilize the capsule, without substantially damaging the function and/or viability of the cells contained therein. Sulfate salts, such as sodium sulfate and potassium sulfate, are preferred, and sodium sulfate is most preferred. The incubation step is carried out in an aqueous solution containing the physiological salt in an amount effective to stabilize the capsules, without substantially damaging the function and/or viability of the cells contained therein as described above. In general, the salt is included in an amount of from about 0.1 or 1 milliMolar up to about 20 or 100 millimolar, most preferably about 2 to 10 millimolar. The duration of the incubation step is not critical, and may be from about 1 or 10 minutes to about 1 or 2 hours, or more (e.g., overnight). The temperature at which the incubation step is carried out is likewise not critical, and is typically from about 4° C. up to about 37° C., with room temperature (about 21° C.) preferred.

IV. Treatment of Diseases or Disorders

Encapsulated cells can be administered, e.g., injected or transplanted, into a patient in need thereof to treat a disease or disorder. In some embodiments, the disease or disorder is caused by or involves the malfunction of hormone- or protein-secreting cells in a patient. In these embodiments, hormone- or protein-secreting cells are encapsulated and administered to the patient. For example, encapsulated islet cells can be administered to a patient with diabetes. In other embodiments, the cells are used to repair tissue in a subject. In these embodiments, the cells form structural tissues, such as skin, bone, cartilage, muscle, or blood vessels. In these embodiments, the cells are preferably stem cells or progenitor cells.

1. Diabetes

The potential of using a bioartificial pancreas for treatment of diabetes mellitus based on encapsulating islet cells within a semi permeable membrane is extensively being studied by scientists. Microencapsulation protects islet cells from immune rejection and allows the use of animal cells or genetically modified insulin-producing cells.

The Edmonton protocol involves implantation of human islets extracted from cadaveric donors and has shown improvements towards the treatment of type 1 diabetics who are prone to hypoglycemic unawareness. However, the two major hurdles faced in this technique are the limited availability of donor organs and the need for immunosuppressants to prevent an immune response in the patient's body.

Several studies have been dedicated towards the development of bioartificial pancreas involving the immobilization of islets cells inside polymeric capsules. The first attempt towards this aim was demonstrated in 1980 by Lim and Sun, Science 210:908 (1980) where xenograft islet cells were encapsulated inside alginate polylysine microcapsules, which resulted in significant in vivo results for several weeks.

The polymers typically used for islet microencapsulation are alginate, chitosan, polyethylene glycol (PEG), agarose, sodium cellulose sulfate and water insoluble polyacrylates.

2. Cancer

The use of cell encapsulated microcapsules towards the treatment of several forms of cancer has shown great potential. One approach undertaken by researchers is through the implantation of microcapsules containing genetically modified cytokine secreting cells. Genetically modified IL-2 cytokine secreting non-autologous mouse myoblasts implanted into mice delay tumor growth with an increased rate of survival of the animals. However, the efficiency of this treatment was brief due to an immune response towards the implanted microcapsules. Another approach to cancer suppression is through the use of angiogenesis inhibitors to prevent the release of growth factors that lead to the spread of tumors. Genetically modified cytochrome P450 expressing cells encapsulated in cellulose sulfate polymers may also be useful for the treatment of solid tumors.

3. Heart Diseases

While numerous methods have been studied for cell administration to enable cardiac tissue regeneration in patients after ischemic heart disease, the efficiency of the number of cells retained in the beating heart after implantation is still very low. A promising approach to overcome this problem is through the use of cell microencapsulation therapy which has shown to enable a higher cell retention as compared to the injection of free stem cells into the heart.

Another strategy to improve the impact of cell based encapsulation technique towards cardiac regenerative applications is through the use of genetically modified stem cells capable of secreting angiogenic factors such as vascular endothelial growth factor (VEGF), which stimulate neovascularization and restore perfusion in the damaged ischemic heart.

4. Liver Diseases

Microencapsulated hepatocytes can be used in a bioartificial liver assist device (BLAD). Acute liver failure (ALF) is a medical emergency which, despite improvements in modern intensive care, still carries a substantial mortality rate. In the most severe cases, urgent orthotopic liver transplantation (OLT) currently represents the only chance for survival. However, the supply of donor organs is limited and an organ may not become available in time. An effective temporary liver support system would improve the chance of survival in this circumstance by sustaining patients until a donor liver becomes available. Furthermore, the known capacity of the native liver to regenerate following recovery from ALF raises the possibility that the use of temporary liver support for a sufficient period of time may even obviate the need for OLT in at least some cases.

In some embodiments, hepatocytes are encapsulated in capsule or microcapsule having an inner core of modified collagen and an outer shell of terpolymer of methyl methacrylate (MMA), methacrylate (MAA) and hydroxyethyl methacrylate (HEMA) (Yin C et al., Biomaterials 24:1771-1780 (2003)).

Cell lines which have been employed or are currently undergoing investigation for use in bioartificial liver support systems include primary hepatocytes isolated from human or animal livers, and various transformed human cells, such as hepatoma, hepatoblastoma and immortalized hepatocyte lines.

The present invention will be further understood by reference to the following non-limiting examples.

The examples demonstrate the formation of core-shell alginate based capsules and microcapsules, which demonstrate that it is possible to isolate the cells within the hydrogel capsules, preventing the cells from being detected by immune cells in the body (Example 1) and that larger, greater than 1 mm in diameter, hydrogel capsules, evoke less of a fibrotic reaction than the same hydrogel capsules having a smaller diameter (Example 2).

EXAMPLES

Example 1: Preparation of Core-Shell Alginate Based Microcapsules

Materials and Methods

Figure 3A:
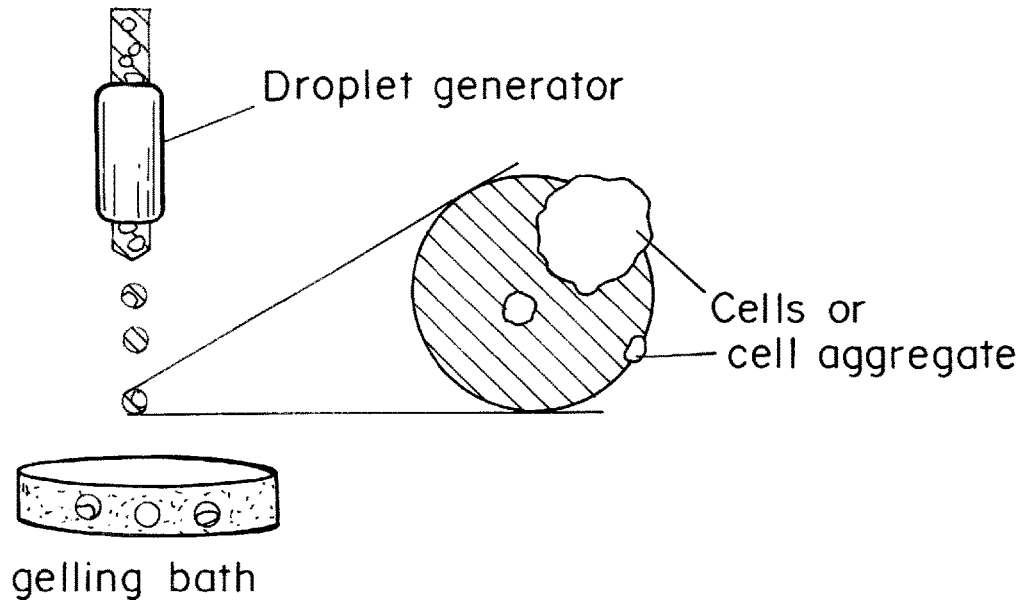
FIGS. 3A and 3B are schematic depictions of a conventional cell encapsulation method in which cells are dispersed within a hydrogel matrix having an outer crosslinked shell (FIG. 3A) and a two-fluid co-axial electro jetting device for forming a hydrogel core containing cells, surrounded by a shell to prevent any of the cells from contacting the outer wall of the capsule and potentially being exposed to immune cells in the host into which the capsule is implanted.
Figure 3B:
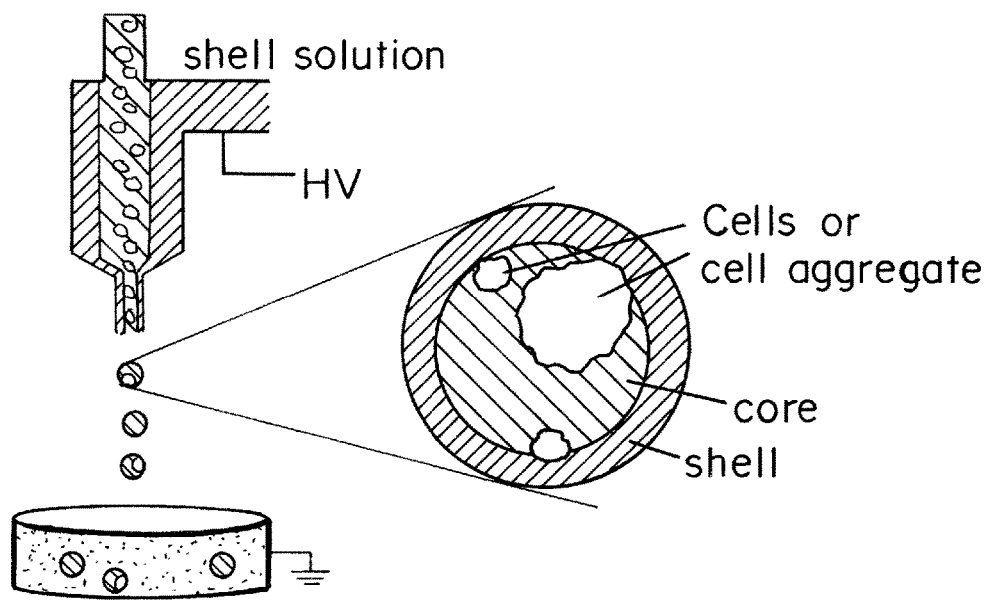

Design of Core-Shell Nozzle and Formation of Core-Shell Capsules:

A type of alginate-based hydrogel microcapsules with core-shell structures using a two-fluid co-axial electro-jetting that is compatible with the current alginate-based cell encapsulation protocols was developed. The composition and thickness of the core and shell can be independently designed and controlled for many types of biomedical applications. FIGS. 3A and 3B are schematic depictions of a conventional cell encapsulation approach (FIG. 3A) and a two-fluid co-axial electro jetting for core-shell capsules and cell encapsulation (FIG. 3B). FIG. 3B shows a schematic of the two-fluid co-axial electro jetting for the fabrication of core-shell capsules and encapsulation of cells or cell aggregates. This two-fluid configuration was used to make core-shell hydrogel capsules and encapsulate living cells.

The shell fluid consists of a cell-free alginate solution, while the core fluid contains the islets or other therapeutic cells. The relatively high viscosity of the two fluids and short interaction time between them prevent their intermixing. Under electrostatic force, microdroplets with core-shell structures are formed and converted to hydrogel capsules in the gelling bath.

First, to demonstrate the formation of core-shell hydrogel capsules, a fluorescently labeled alginate was used to form the shell and a non-labeled alginate was used to form the core. The thicknesses of the core and shell can be controlled by simply tuning their respective flow rates. For cell encapsulation, the size of the core can then be designed based on the desired mass of cells per capsule, while that of the shell can be adjusted according to the requirements of mechanical strength and mass transfer. The compositions of the core and shell are also adjustable. This allows independent optimization of the material in direct contact with the encapsulating cells and the one adjacent to the host immune system when transplanted. For example, an anti-inflammatory drug or an imaging contrast reagent (e.g., iron oxide nanoparticles) can be loaded in the shell without contacting the cells in the core. It is also possible to put a different material such as Matrigel as the core inside the alginate shell. The core material, which may not be able to form mechanically robust capsules alone, can then provide a preferred local environment for the encapsulated cells.

The design of the co-axial nozzle was critical to the stable formation of uniform core-shell structures of the capsules, and complete encapsulation of islets. First, the nozzle must be concentric; any eccentricity may cause non-uniform flow of the shell fluid surrounding the core fluid, disturbing the core-shell structure. Second, the nozzle must be designed in a way that the flow of the shell fluid inside the nozzle is uniform around the core tube. Third, the inner diameter (ID) of the core tube must accommodate the sizes of islets. The co-axial nozzle has a core tube with an ID of 0.014" and an outer diameter (OD) of 0.022" and a shell tube with an ID of 0.04" and an OD of 0.0625". The length of the shell tube that protrudes from the nozzle body is 0.5" and was tapered at the outlet tip. The core tube was placed 100 microns inward relative to the shell tube at the outlet. The flow rates of the core and shell fluids were independently adjusted by separate syringe pumps. The voltage was 6.2 kV and the distance between the nozzle tip and the surface of gelling solution was 1.8 cm.

To optimize encapsulation, the solution concentration of alginate with given molecular weight must be optimized. If both the concentrations of the core and shell solutions are too small, there will be significant intermixing between the core and shell solutions leading to non-uniform core-shell structures. For the PRONOVA® SLG20 alginate (Mw approximately 75-220,000, FMC BIOPOLYMER®), it was found the optimal concentration ranges were from 0.8% (w/v) to 2% (w/v). All alginate solutions were at 1.4% (w/v) and the MATRIGEL® (BD Biosciences) was used at 4 mg/mL in a 4° C. cold room to avoid gelling prior to encapsulation. Besides the properties of the core and shell solutions, optimization of operating parameters was also important to obtain ideal encapsulation. Typical flow rates were 0.005 mL/min to 0.1 mL/min for the core flow and 0.1 mL/min to 0.5 mL/min for the shell flow.

Rat Islet Isolation and Purification:

Sprague-Dawley rats from Charles River Laboratories weighting approximately 300 grams were used for harvesting islets. All rats were anesthetized by a 1:20 Xylazine (10 mg/kg) to Ketamine (150 mg/kg) injection given intraperitoneally, and the total volume of each injection was 0.4-0.5 mL depending on the weight of rat. Isolation surgeries were performed. Briefly, the bile duct was cannulated and the pancreas was distended by an in vivo injection of 0.15% Liberase (Research Grade, Roche) in RPMI 1640 media solution. Rats were sacrificed by cutting the descending aorta and the distended pancreatic organs were removed and held in 50 mL conical tubes on ice until the completion of all surgeries. All tubes were placed in a 37° C. water bath for a 30 minute digestion, which was stopped by adding 10-15 mL of cold M199 media with 10% heat-inactivated fetal bovine serum and lightly shaking. Digested pancreases were washed twice in the same aforementioned M199 media, filtered through a 450 μm sieve, and then suspended in a Histopaque 1077 (Sigma)/M199 media gradient and centrifuged at 1,700 RCF at 4° C. Depending on the thickness of the islet layer that was formed within the gradient, this step was repeated for higher purity islets. Finally, the islets were collected from the gradient and further isolated by a series of six gravity sedimentations, in which each supernatant was discarded after four minutes of settling. Purified islets were hand-counted by aliquot under a light microscope and then washed three times in sterile 1× phosphate-buffered saline. Islets were then washed once in RPMI 1640 media with 10% heat-inactivated fetal bovine serum and 1% penicillin/streptomycin, and cultured in this media overnight for further use.

Liver Tissue Homogenization and Encapsulation:

Liver was obtained from sacrificed rats by dissecting the liver from the hepatic portal, system vessels and connective tissue. It was placed into a 0.9% NaCl solution and minced using surgical forceps and scissors in a petri dish. These pieces were washed with 0.9% saline twice to remove blood and then dissociated using a gentle MACS Dissociator (Miltenyi Biotec). After dissociation, the tissue sample was filtered through a 100 μm cell strainer and subsequently a 40 μm one. This filtration was repeated once more to obtain liver tissue cells for encapsulation. For single-fluid encapsulation, 0.06 mL dissociated liver tissue cells were dispersed in 4.5 mL 1.4% SLG20 alginate solution. For the two-fluid coaxial encapsulation, 0.06 mL dissociated liver cells were dispersed in 0.5 mL 1.4% SLG20 alginate solution that was used as the core fluid. A separate 4 mL 1.4% alginate solution was used as the shell.

Islets Encapsulation and Transplantation:

Immediately prior to encapsulation, the cultured islets were centrifuged at 1400 rpm for 1 minute and washed with Ca-Free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH approximately 7.4, osmotic pressure approximately 290 mOsm). After the wash, the islets were centrifuged again and all supernatant was aspirated. The islet pellet was then re-suspended in a 1.4% solution of SLG20 alginate dissolved in 0.8% NaCl solution at desired islet number density. In the case of the regular capsules, 0.27 mL alginate solution was used for every 1000 islets. For the core-shell capsules, 0.03 mL solution for every 1000 islets was used as the core fluid. Another 0.24 mL 1.4% alginate solution without islets was used as the shell fluid. The flow rate for the shell was 0.2 mL/min and that for the core was 0.025 mL/min. For the same number of islets, the total volume of the alginate solution used in both regular encapsulation and core-shell encapsulation was therefore the same. Capsules were crosslinked using a $BaCl_2$ gelling solution (20 mM BaCl2, 250 mM D-Mannitol, 25 mM HEPES, pH~7.4, osmotic pressure approximately 290 mOsm) Immediately after crosslinking, the encapsulated islets were washed 4 times with HEPES buffer and 2 times with RPMI Medium 1640 and cultured overnight at 37° C. for transplantation. As the islets had variable sizes (50-400 µm) and there was an inevitable loss of islets during the encapsulation process, the total number of encapsulated islets were recounted and converted into islet equivalents (IE, normalized to 150 µm size) prior to transplantation.

Immune-competent male C57BL/6 mice were utilized for transplantation. To create insulin-dependent diabetic mice, healthy C57BL/6 mice were treated with Streptozocin (STZ) by the vendor (Jackson Laboratory, Bar Harbor, Me.) prior to shipment to MIT. The blood glucose levels of all the mice were retested prior to transplantation. Only mice whose non-fasted blood glucose levels were above 300 mg/dL for two consecutive days were considered diabetic and underwent transplantation. The mice were anesthetized using 3% isofluorane in oxygen and maintained at the same rate throughout the procedure. Preoperatively, all mice received a 0.05 mg/kg dose of buprenorphine subcutaneously as a pre-surgical analgesic, along with 0.3 mL of 0.9% saline subcutaneously to prevent dehydration. The abdomens of the mice were shaved and alternately scrubbed with betadine and isopropyl alcohol to create a sterile field before being transferred to the surgical field. A 0.5 mm incision was made along the midline of the abdomen and the peritoneum was exposed using blunt dissection. The peritoneum was then grasped with forceps and a 0.5-1 mm incision was made along the linea alba. A desired volume of capsules with predetermined number of islet equivalents were then loaded into a sterile pipette and transplanted into the peritoneal cavity through the incision. The incision was then closed using 5-0 taper tipped polydioxanone (PDS II) absorbable sutures. The skin was then closed over the incision using a wound clip and tissue glue.

All animal protocols were approved by the MIT Committee on Animal Care and all surgical procedures and post-operative care were supervised by MIT Division of Comparative Medicine veterinary staff.

Confocal Imaging of Encapsulated Islets:

Pancreatic islets were stained with Hoechst dye (2 µg/mL) and encapsulated in fluorescent, regular capsules or core-shell capsules with a fluorescently labeled shell. The capsules were placed on chambered glass coverslips (LabTek) and allowed to settle. The encapsulated islets were then imaged under a 10× objective using a Laser Scanning Confocal Microscope 710 (LSM710). Multiple confocal slices were imaged from bottom to top of sample to construct a Z-stack. An orthogonal image and a 3D rendering were performed using LSM browser software to visualize the islet-containing capsules.

Blood Glucose Monitoring:

Blood glucose levels were monitored three times a week following the transplant surgery. A small drop of blood was collected from the tail vein using a lancet and tested using a commercial glucometer (Clarity One, Clarity Diagnostic Test Group, Boca Raton, Fla.). Mice with unfasted blood glucose levels below 200 mg/dL were considered normoglycemic. Monitoring continued until all mice in the experimental group had returned to a hyperglycemic state at which point they were euthanized.

Results

Better cell encapsulation using core-shell capsules was demonstrated using both homogenized rat liver tissue cells and rat pancreatic islets. Microscopic images for both regular capsules and core-shell capsules containing islets show a relatively low volume of alginate solution per islet (i.e., 0.27 mL solution for every 1000 islets) used to minimize the total volume of capsules for transplantation. This is approximately a third of the volume that is typically used (deVos et al., Transplantation 1996, 62, 888). For crosslinking, a $BaCl_2$ solution (deVos et al., Transplantation 1996, 62, 888) was used and the average capsule sizes were both around 500 µm. For regular capsules, the islets were randomly located within the capsules and islets protruding outside were frequently observed. In contrast, the islets in the core-shell capsules were fully encapsulated. The core-shell structure of the capsules was demonstrated by using a fluorescent alginate in the shell and a non-fluorescent alginate in the core. Fluorescent images where the islets were stained blue (i.e. nuclei staining) showed that in some cases the islets were close to the core-shell interface but still completely encapsulated due to the additional shell layer. It is important to note that a confocal microscopy technique was used to confirm the full encapsulation. Conventional microscopic examination may be misleading as the relatively dense islet mass may fall at the bottom of the capsule and in line with the objective. In traditionally formed alginate capsules, the islets appeared fully encapsulated under conventional light microscope. The z-series and orthogonal views using confocal microscopy revealed however the islets were partially exposed outside the capsules. In contrast, the core-shell capsules fully enclosed the islets as viewed from all three directions. Quantitatively, based on examinations of a number of islets-containing capsules using confocal microscopy, the regular capsules had about 30% with protruding islets while the core-shell capsules had none. The hydrogel microcapsules with core-shell structures were formed with a shell of an alginate partially modified with FITC, while the core is unlabeled alginate or Matrigel. The thicknesses of the shell and the core are controlled by tuning their respective flow rates: (a) 0.1 mL/min and 0.1 mL/min; (b) 0.15 mL/min and 0.05 mL/min; (c) 0.2 mL/min and 0.02 mL/min. The compositions of the core and shell can also be independently controlled. (d) The shell alginate contains particles of an anti-inflammatory drug, curcumin. The drug particles are self-fluorescent. The shell is fluorescent alginate and the core is non-fluorescent Matrigel.

Streptozotocin (STZ)-induced diabetic mouse model (Brodsky et al., Diabetes 1969, 18, 606) was used to evaluate the functionality of the coaxially encapsulated islets and compare the efficacy with regular capsules. A comparison was conducted of islets encapsulated in regular capsules and core-shell capsules. 3D reconstructed confocal fluorescent images of islets encapsulated in core-shell capsules showed the islets were stained blue, while the shell was labeled green.

Figure 4A:
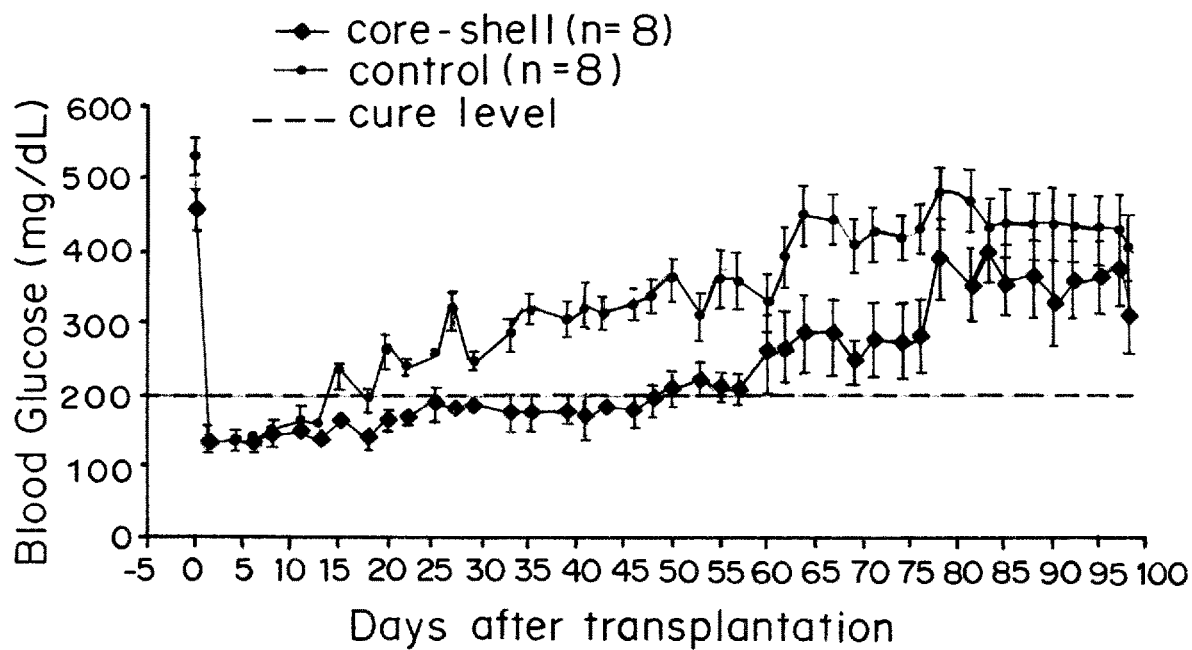
FIGS. 4A and 4B are graphs comparing control, regular capsules and core-shell capsules in treating Type I diabetes.
Figure 4B:
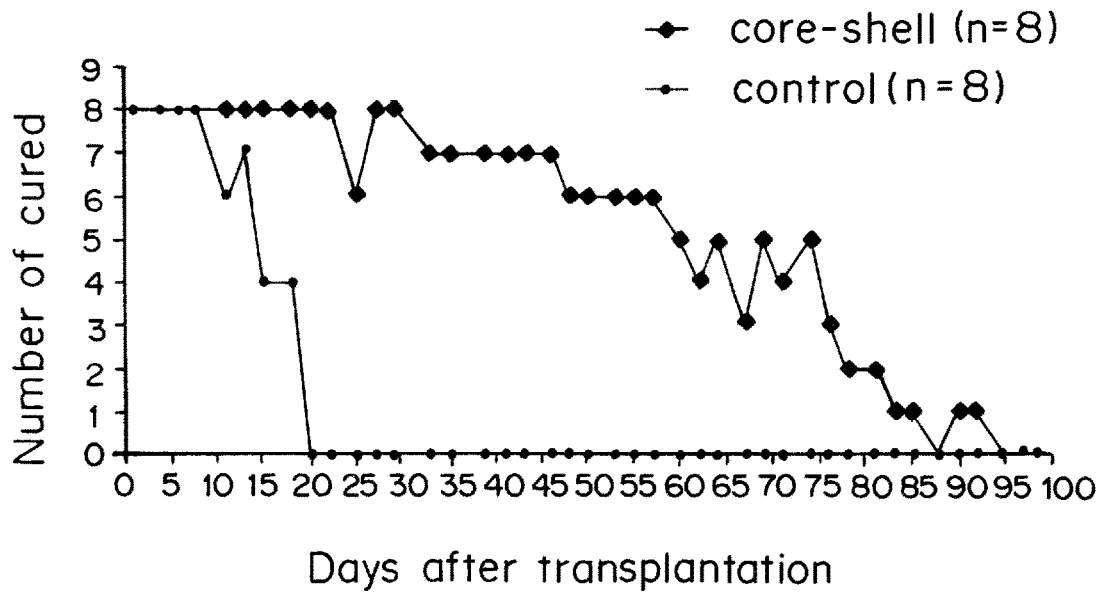

Encapsulated rat islets were transplanted into the peritoneal cavity of the diabetic mice and their blood sugar was measured. FIG. 4A shows the blood glucose level of the mice as a function of days post-transplantation for both core-shell capsules (diamonds) and regular (circles) capsules. For both types of capsules, a density of 1000 islets per 0.27 mL alginate solution was used and each mouse was transplanted with 500 islet equivalents (normalized to 150 µm size). Mice with blood glucose below 200 mg/dL are considered normoglycemic (Kim et al., Lab Chip 2011, 11, 246). A couple of days after transplantation, all diabetic mice became normoglycemic, as expected. However, differences between the two types of capsules started to appear after about 2 weeks, as demonstrated in FIG. 4B. The average blood glucose level for the mice receiving regular capsules went back above 200 mg/dL by 15 days, and that of the mice receiving core-shell capsules remained below 200 mg/dL up to 50 days. FIG. 4Bb shows the percentage of normoglycemic mice over days following transplantation. Regular capsules in all mice failed to control the diabetes by 20 days, while the core-shell ones in some of the mice did not fail until about 80 days after transplantation, indicating that the core-shell capsules improved the treatment significantly compared with the regular capsules.

In summary, hydrogel microcapsules with core-shell structures and their use for improved cell encapsulation and immuno-protection have been made. Better islet encapsulation using the core-shell capsules at a reduced material volume per islet was demonstrated. Improved immune-protection was achieved in a single step by simply confining the cells or cell aggregates in the core region of the capsules. Both the core-shell structure and better encapsulation were confirmed by confocal microscopy. Using a type I diabetic mouse model, it was shown that the core-shell capsules encapsulating rat islets provided a significantly better treatment than the currently used, regular capsules.

Islet microencapsulation represents a promising approach to treat Type I diabetes and has been a topic of intensive research for decades (Bratlie et al., Adv. Healthcare Mater. 2012, 1, 267). The results from different research groups were often inconsistent. Islet quality and material properties such as biocompatibility are certainly critical factors that affect the outcome of treatment. The quality of encapsulation could also influence the results and cause inconsistency. The core-shell capsules can be made in a single step using the same encapsulation protocols that have been used to make the regular capsules and do no harm to islets. In addition to providing better immuno-protection, the opportunity to control the compositions of the shell and the core provide additional opportunities in microencapsulation. Examples include the replacement of the alginate in the core with a different material that may enhance long-term islet survival. In addition, insulin-producing cells derived from stem cells (Calne et al, Nature Reviews Endocrinology 2010, 6, 173) or adult cells (Zhou, et al., Nature 2008, 455, 627) provide a great alternative to islets. The core-shell capsules allow not only improved encapsulation but also greater freedom in the designs of the encapsulating material in the shell and that in direct contact with the cells in the core.

Example 2: Preparation of Large Two-Layer Hydrogel Capsules (Diameter >1 mm) for Encapsulation of Therapeutic Cells and Cell Aggregates Materials and Methods The method of encapsulation includes two general steps: (a) forming droplets of alginate solution containing islets and (b) conversion of the droplets into hydrogel capsules. Mechanical or electrostatic forces can be used to control the droplet or capsule sizes. The islets can be randomly distributed within the capsules. The islets can also be introduced in the shell region of the capsules to facilitate the mass transfer. This can be achieved by using a two-fluid encapsulation approach where one stream of alginate solutions containing islets serves as the shell fluid and a separate stream of cell-free alginate solution flows in the core. Additional components such as an anti-inflammatory drug can also be incorporated into the core.

Two types of large (diameter >1 mm) alginate hydrogel capsules for islets encapsulation were prepared. In the first, islets were dispersed randomly within the capsules. In the second, islets were purposely placed in the shell region of the capsules.

1.5 mm capsules encapsulating rat islets were injected into STZ-induced diabetic mice. The 500 µm capsules were used as the control and 500 IE's were used for both sizes of capsules.

Results

The large size (diameter >1 mm) capsules were much less fibrotic and provided much longer cure than conventional (0-500 µm) capsules. The 500 µm capsules were used as the control and 500 IE's were used for both sizes of capsules. All 5 mice in the 500 µm capsule group failed by 43 days (blood glucose above 200 mg/dl for 3 consecutive measurements), while the large capsules lasted much longer. All the 5 mice in the 500 µm capsule group failed by 43 days (i.e. BG above 200 mg/dl for 3 consecutive measurements), while the large capsules lasted much longer. One of the 5 mice failed at 43 days, one failed at 75 days, another one failed at 146 days and the rest two remained cured at 196 days when the experiment was stopped.

In a separate follow-up study again with 500 IE's, all eight mice in the 500 µm capsule group failed by 35 days, while in the 1.5 mm capsule group, 1 out of 6 failed at 28 days, 1 failed at 105 days, 1 failed at 134 days, another failed at 137 days, and 2 remaining ones stayed cured at 175 days when the experiment was stopped.

Figure 5A:
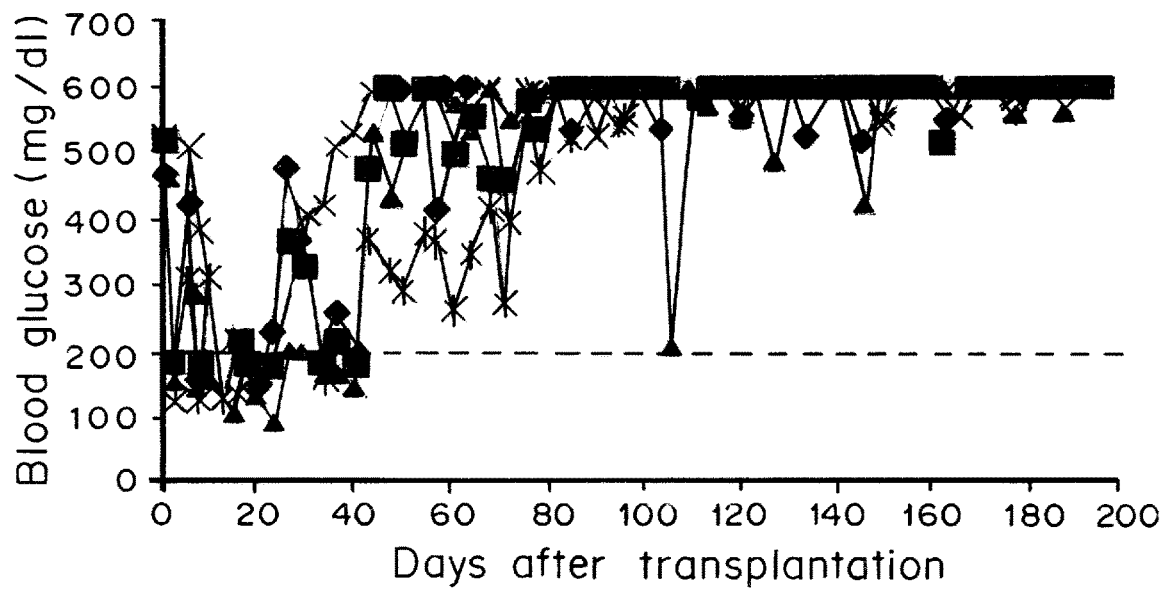
FIGS. 5A and 5B are graphs comparing blood glucose levels in STZ-induced C57BL/6 diabetic mice implanted with 500 μm hydrogel capsules containing islet cells (FIG. 5A) and 1.5 mm alginate capsules encapsulating rat islets (500 IE's) (FIG. 5B).
Figure 5B:
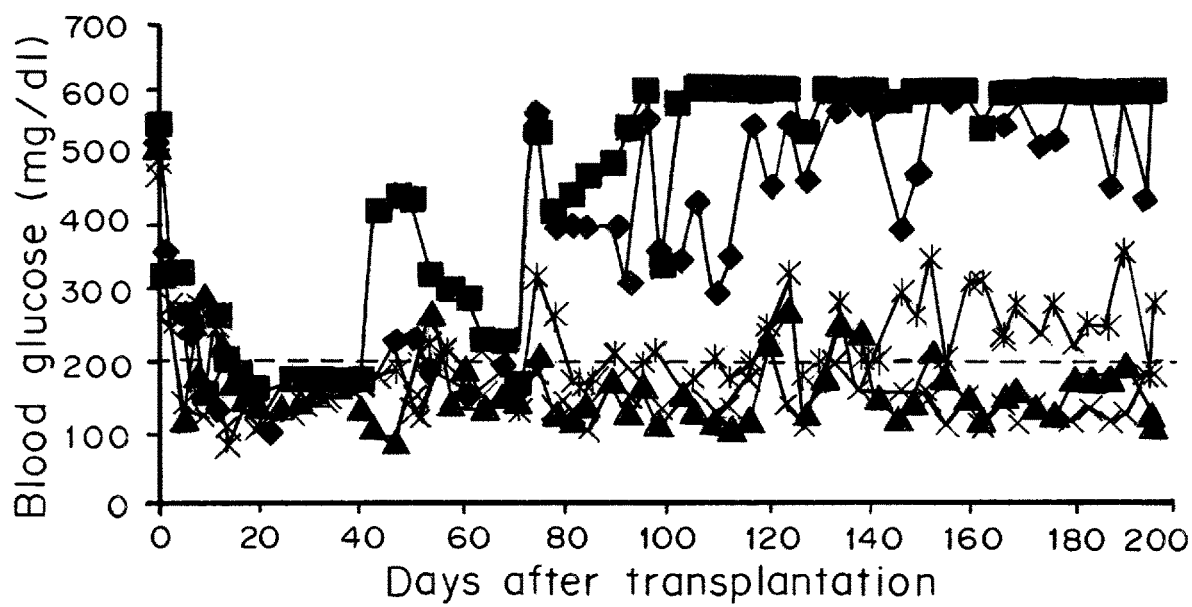

See FIG. 5A for 500 micron capsule and FIG. 5B for 1.5 mm capsules.

Analysis of retrieved capsules revealed that the 500 µm capsules were all fibrosed and clumped but the 1.5 mm capsules were much less fibrotic.

In summary, large hydrogel capsules, with diameter larger than 1 mm, were made by encapsulating cells or cell aggregates, such as islets using materials such as alginate hydrogel. Islets encapsulated in alginate hydrogel capsules can be transplanted to treat Type I diabetes without the use of immunosuppressive drugs. One major challenge is the fibrotic reactions to the capsules upon transplantation, which eventually leads to necrosis of islets and failure of transplant. The typical diameter of currently used capsules is relatively small, less than 1 mm. It has been discovered that larger capsules have less fibrosis and could therefore have better disease outcomes for clinical uses.

Figure 6:
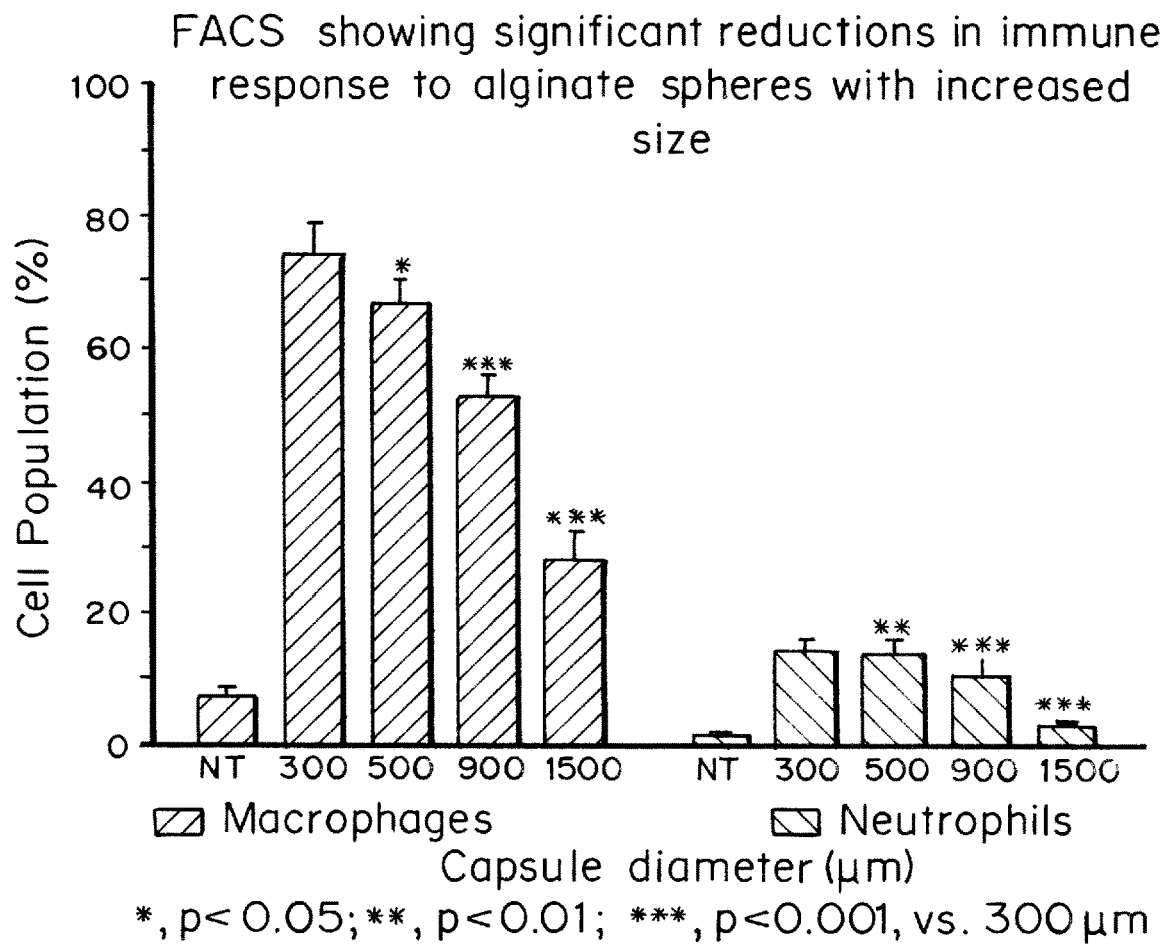
FIG. 6 is a graph of immune response (percent of cell population made up of macrophages or neutrophils) in empty capsules of different sizes. Capsules of 300 μm, 500 μm, 900 μm, and 1500 μm were assessed.

Example 3: Comparison of Fibrotic Effects on Large (Diameter >1 mm) and Small (Diameter <1 mm) Hydrogel Capsules The disclosed two or three layer hydrogel capsules are useful for sensor or controlled drug release applications. In some embodiments, the capsules are designed to resist foreign body responses. General characteristics of preferred capsules include: a size larger than 1 mm and a spherical shape; a smooth surface with no straight edges; made from hydrophilic material; and capsule can be porous, with pores preferably be less than 1 µm in size. Capsules larger than 1 mm effectively resist macrophage cell adhesion. For example, macrophage coverage can be less than 30% of total capsule surface area. This example shows the reduced fibrotic effect on capsules larger than 1 mm. Capsules larger than 1 mm effectively resist macrophage and neutrophil adhesion and decrease macrophage and neutrophil recruitment (FIG. 6). For example, macrophage and neutrophil levels were assayed by FACS in fibrotic tissue associated with the capsules and was reduced to less than 30% of the levels observed with smaller 300 um capsules (FIG. 6). Larger core-shell (multi-layer alginate capsules) were produced using the dual nozzle electro-spray method (illustrated in FIG. 1), and they also showed similar reduction in macrophage/neutrophil recruitment and adhesion. This holds true for capsules taken from completely healthy as well as STZ-induced diabetic C57BL/6 mice, throughout many timepoints post-transplantation (e.g., 7, 14, and 28 days, as well as at 1, 6 months, and 1 year). Furthermore, fibrosis was measured by visual inspection of cellular adhesion and fibrotic overgrowth upon phase contrast/brightfield imaging, as well as by confocal imaging and western blotting for F-actin (cell overgrowth marker) and alpha smooth muscle actin (fibrosis marker). qPCR was also used to determine relative levels of collagen (1A1) deposition. These examples show the reduced fibrotic effect on capsules larger than 1 mm.

Empty capsules (capsules without encapsulated cells) of different sizes were produced using SLG100 alginate (PRONOVA). The capsules were transplanted intraperitoneally in C57BL/6 mice and incubated for 2 weeks before retrieval and analysis of host rejection responses (i.e., immune inflammation and fibrosis), as determined by FACS analysis, qPCR, confocal imaging, and/or western blotting. Phase contrast images were used to assess relative levels of cellular overgrowth and fibrosis across n=5 individuals per treatment group (i.e., capsule size). Capsules of 300 µm and 500 µm were significantly more fibrotic after 28 days than 1100 µm capsules.

Capsules of uniform sizes: small (300 µm), medium (500 µm), and large (1500 µm), were produced using the electrospray technique and incubated intraperitoneally in C57BL/6 mice and retrieved after 14 days for analysis. The capsules were examined using several measures of fibrosis (FACS analysis, qPCR, confocal imaging, and/or western blotting). Capsules of 300 µm and 500 µm showed significantly more fibrosis than 1500 µm capsules in brightfield and confocal imaging.

Figure 7:
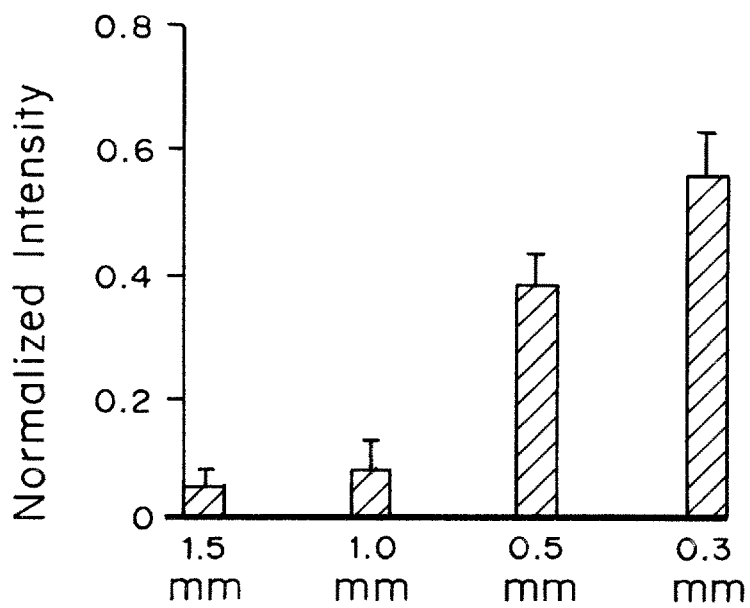
FIG. 7 is a graph of normalized signal intensity of smooth muscle actin and β-actin associated with capsules of 0.3 mm, 0.5 mm, 1 mm, and 1.5 mm determined by Western blot.

The immune response to capsules of different sizes was assessed by measuring the percentage of immune cell populations comprised of either macrophages or neutrophils (FIG. 6). Capsules of 300 µm, 500 µm, 900 µm, and 1500 µm were incubated for 14 days intraperitoneally in immune competent C57BL/6 mice, before samples were retrieved for analysis by FACS. The percentage of macrophages was high for the 300 µm capsules and steadily declined as the capsule size increased. The percentage of neutrophils was high for the 300 µm, 500 µm and 900 µm capsules and dropped to nearly the control level for the 1500 µm capsules. Protein from retrieved capsules of 0.3 mm, 0.5 mm, 1 mm, and 1.5 mm capsules were also analyzed by western blotting. Western Blotting of smooth muscle actin (SMA) and β-actin confirmed the same trend of reduced fibrosis with increasing capsule size. The amount of smooth muscle actin and β-actin associated with the different capsule sizes were determined by Western blot. The signal for smooth muscle actin was normalized against the signal for β-actin. The level of smooth muscle actin was low for the 1.5 mm and 1 mm capsules but was much higher for the 1.5 mm and 1.0 mm capsules (FIG. 7).

Figure 8:
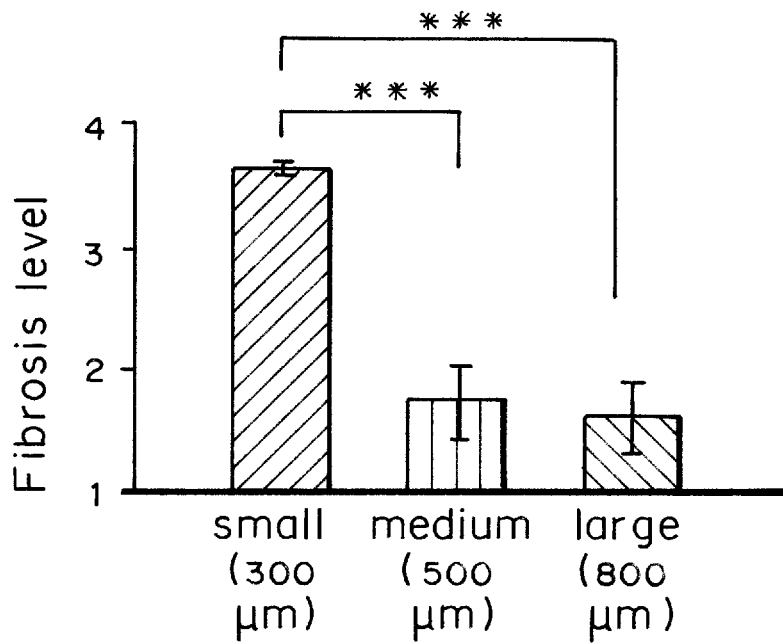
FIG. 8 shows graphs of the fibrosis level for capsules of 300 μm, 500 μm, and 800 μm normalized for surface area of the capsules (FIG. 8, top) or for volume of the capsules (FIG. 8, bottom).
Figure 8:
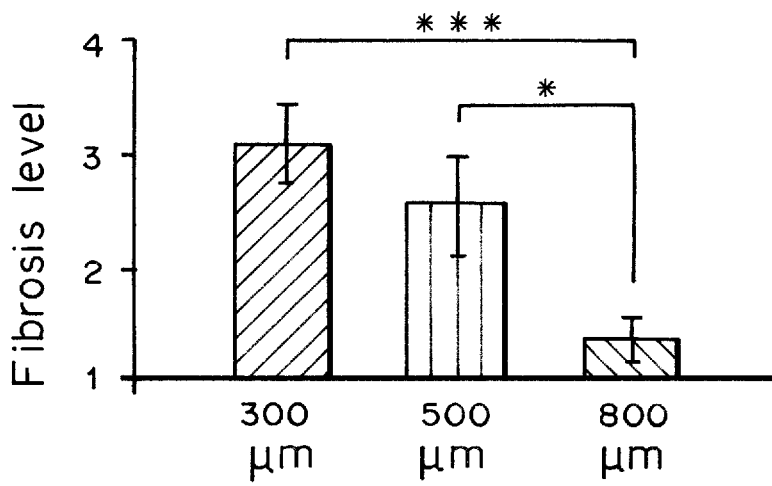
Figure 9A:
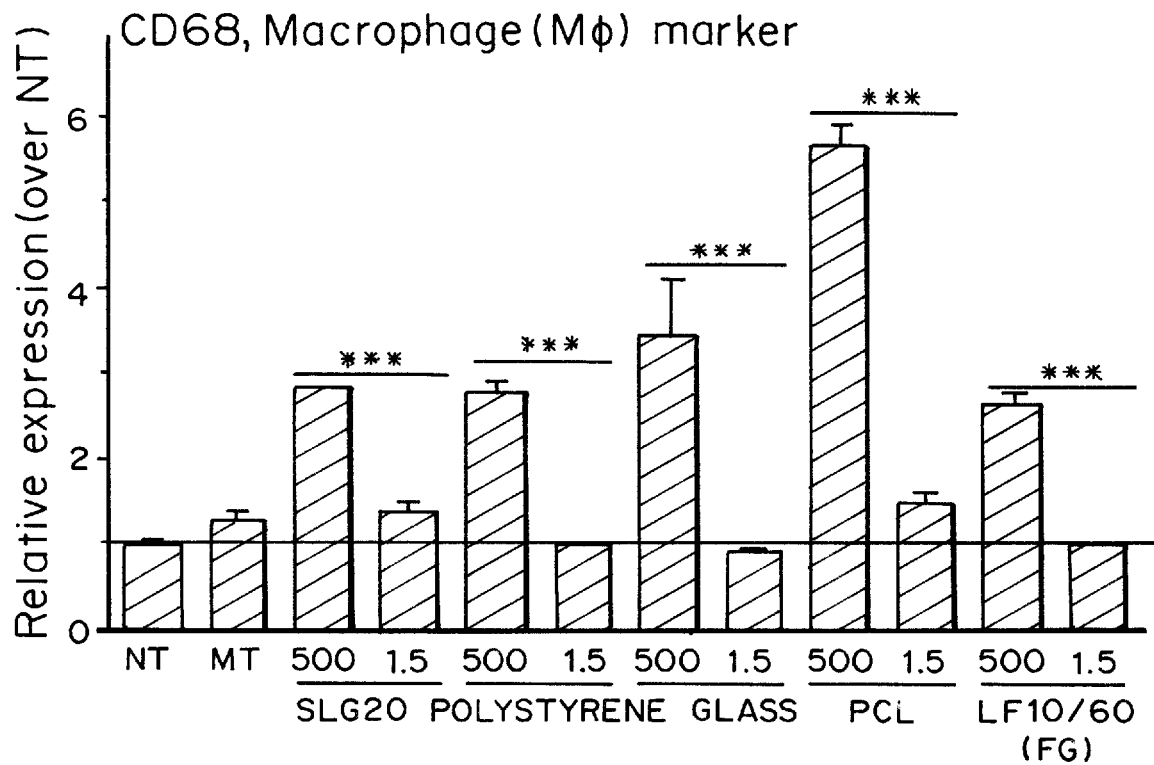
FIGS. 9A-9D are graphs of the relative expression of fibrosis markers in capsules of 500 μm and 1500 μm were made of SLG20 alginate (PRONOVA®), polystyrene, glass, polycaprolactone (PCL), and LF10/60 alginate (FMC BIOPOLYMER®). Fibrosis was measured using CD68 (macrophage marker.
Figure 9B:
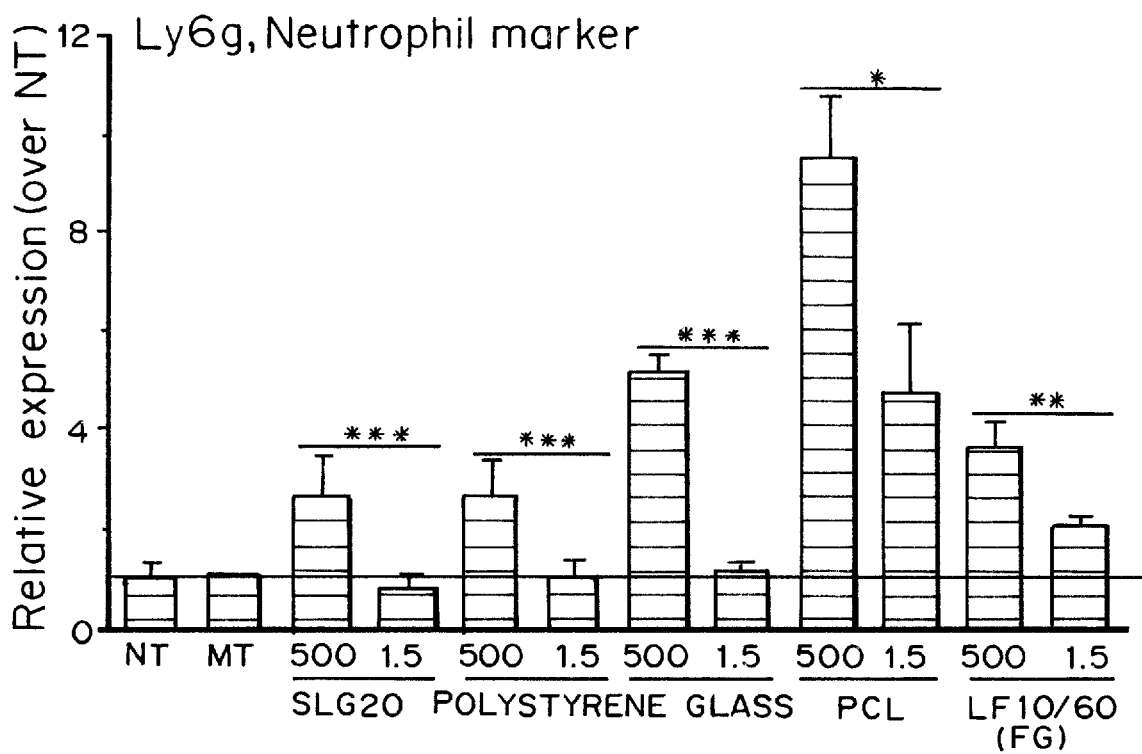
Figure 9C:
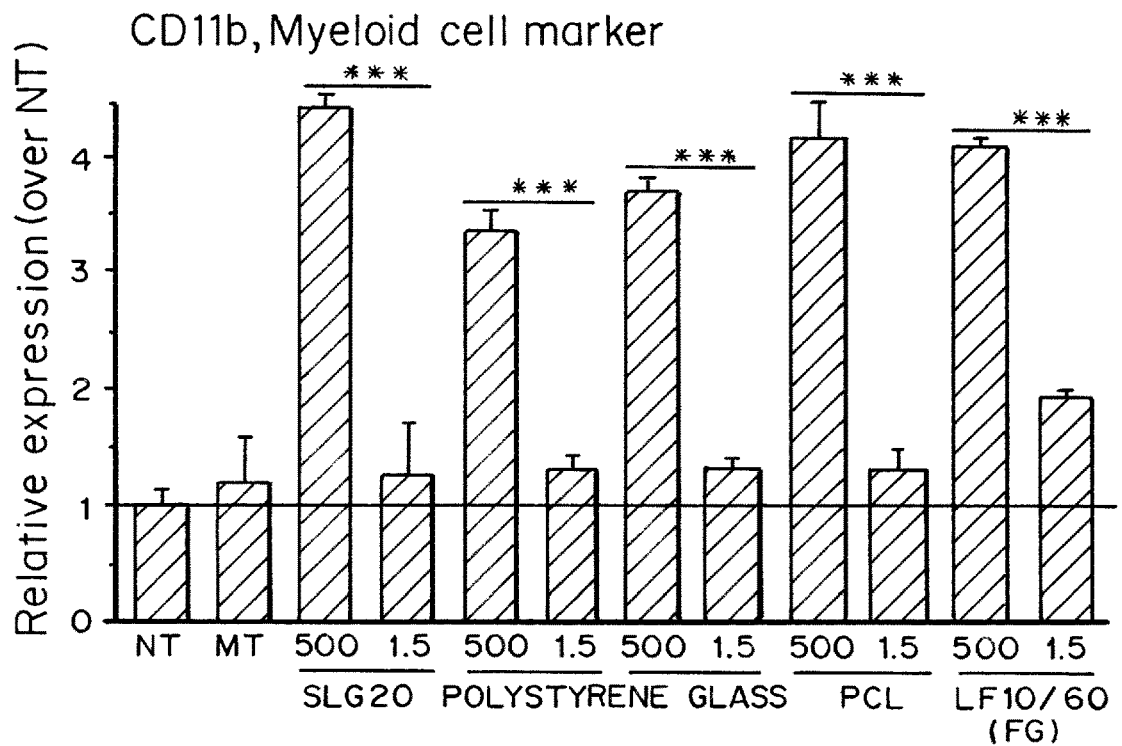
Figure 9D:
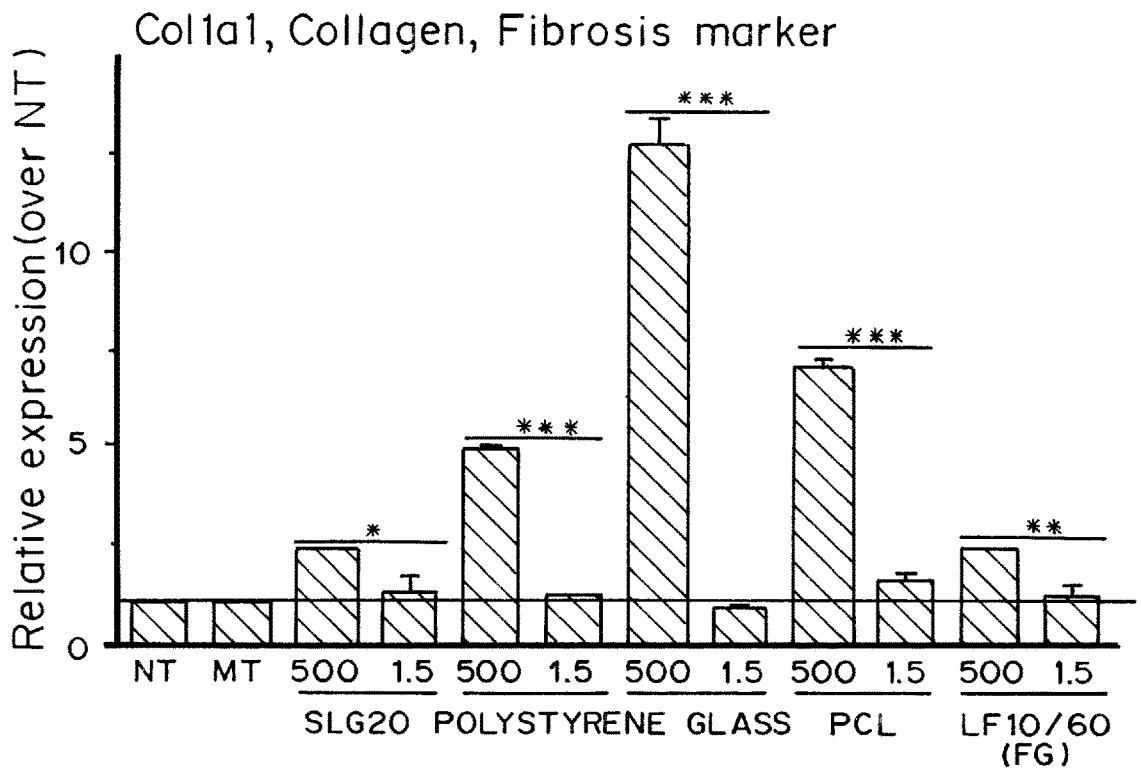

The reduced fibrosis effect remains evident even when the surface area or volume of the capsules is normalized. Capsules of 300 µm, 500 µm, and 800 µm were incubated intraperitoneally in C57BL/6 mice, retrieved after 14 days, and imaged using phase contrast microscopy. The amount of fibrosis observed was normalized for surface area of the capsules (FIG. 8, top) or for volume of the capsules (FIG. 8, bottom). In both cases, the measure of fibrosis was greatest for the 300 µm capsules and lowest for the 800 µm capsules. Reduced fibrosis for large capsules versus small capsules was still apparent when large capsules (1000 µm) were tested at 9 times the volume of small capsules (300 µm).

The reduced fibrosis effect of large capsules remains evident across a variety of materials. Capsules of 500 µm and 1500 µm were made of SLG20 alginate (PRONOVA®), polystyrene, glass, polycaprolactone (PCL), LF10/60 alginate (FMC BIOPOLYMER®), and large 2000 µm Teflon spheres. The capsules were incubated in C57BL/6 mice for 14 days, and analyzed by various techniques (i.e., qPCR and FACS). Fibrosis was measured using CD68 (macrophage marker), Ly6g (neutrophil marker), CD11b (myeloid cell marker), and Col1a1 (fibrosis marker) were assayed by qPCR. With only a couple of exceptions, the markers were expressed at or near the control levels in all 1500 µm capsules and significantly above the control level for all 500 µm capsules (FIG. 9). The exceptions were Ly6g expression for polycaprolactone (PCL) capsules and LF10/60 alginate capsules and CD11b expression for LF10/60 alginate capsules. In each of these cases, expression of the marker was higher than the control for the 1500 µm capsule (but still significantly less than the expression level for the 500 µm capsule.

Figure 10A:
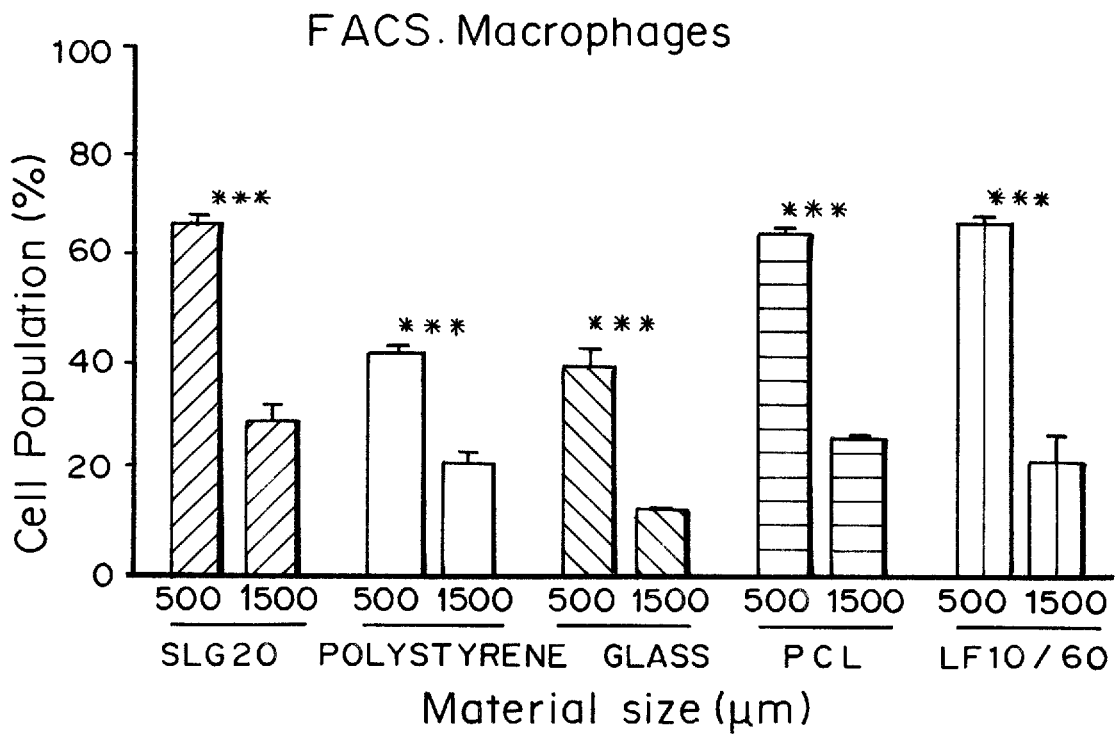
FIGS. 10A and 10B are graphs of immune response (percent of cell population made up of macrophages (FIG. 10A) or neutrophils (FIG. 10B)) in capsules of 500 μm and 1500 μm made of different materials. The capsules were made of SLG20 alginate (PRONOVA®), polystyrene, glass, polycaprolactone (PCL), and LF10/60 alginate (FMC BIOPOLYMER®).
Figure 10B:
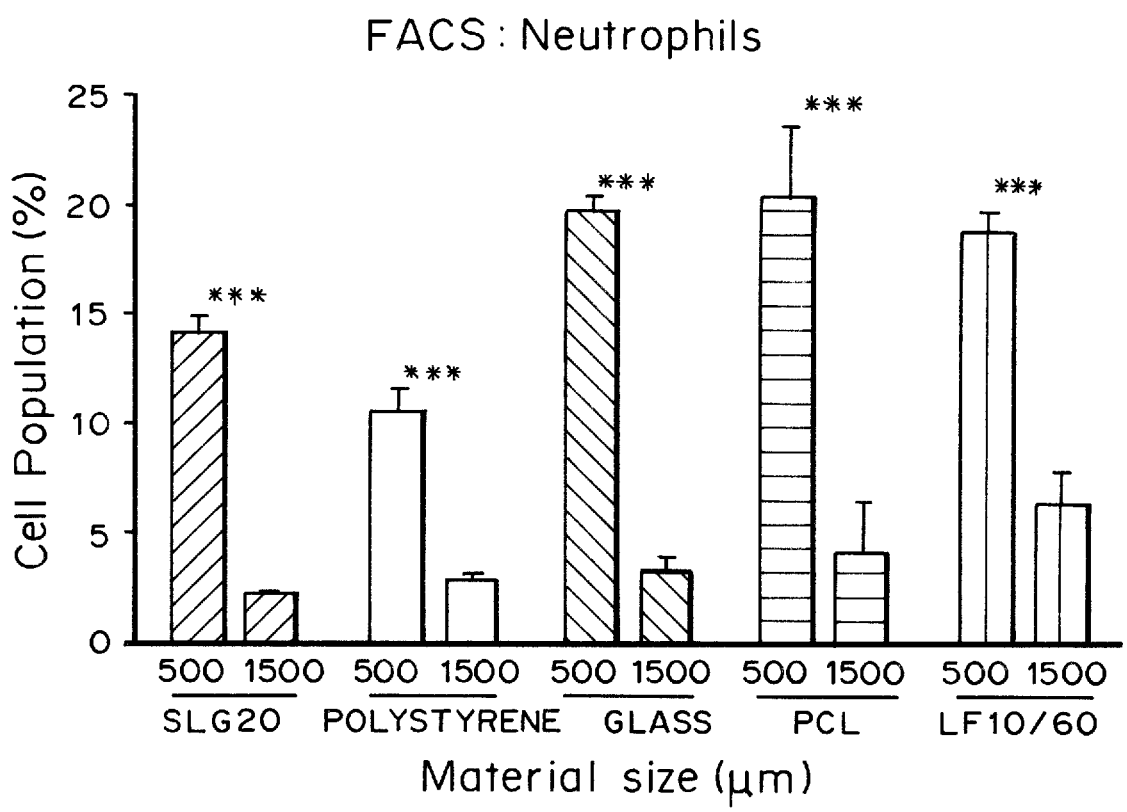

The immune response to capsules of 500 µm and 1500 µm made of these different materials was also assessed at the cellular level by measuring the percentage of cell population composed of macrophages and neutrophils by FACS (FIG. 10). The capsules were made of SLG20 alginate (PRONOVA®), polystyrene, glass, polycaprolactone (PCL), and LF10/60 alginate (FMC BIOPOLYMER®). The capsules were incubated in C57BL/6 mice for 14 days, and analyzed by various techniques (i.e., qPCR and FACS). In every case the percentage of macrophages and the percentage of neutrophils was significantly higher for the 500 µm capsules than for the 1500 µm capsules (FIG. 10).

Modifications and variations of the present invention will be further understood by reference to the following claims. All references cited herein are specifically incorporated by reference.

We claim:

1. A population of hydrogel capsules consisting essentially of hydrogel capsules that have a mean diameter, as measured by confocal microscopy, of at least 1.1 mm and less than 8 mm, wherein the hydrogel capsules:
   (i) encapsulate mammalian cells selected from the group consisting of mammalian secretory cells, mammalian metabolic cells, mammalian structural cells and aggregates thereof;
   (ii) consist of two hydrogel layers and an optional acellular core as a third layer, and wherein the two hydrogel layers contain a first inner, hydrogel layer comprising the mammalian cells, and a second outer, cell-free hydrogel layer, and wherein the first and second hydrogel layers independently have a three-dimensional open-lattice polymeric structure formed by crosslinking of a biocompatible hydrogel forming polymer; and
   (iii) are spheres or ellipsoids having semi-principal axes within 10% of each other.

2. The population of hydrogel capsules of claim 1, wherein the mean diameter is at least 1.2 mm and less than 8 mm.

3. The population of hydrogel capsules of claim 1, wherein the mean diameter is at least 1.5 mm and less than 8 mm.

4. The population of hydrogel capsules of claim 1, wherein the mean diameter is between 1.5 mm and 6 mm, 1.5 mm and 5 mm, 1.5 mm and 4 mm, 1.5 mm and 3 mm, or 1.5 mm and 2 mm.

5. The population of hydrogel capsules of claim 1, wherein the biocompatible, hydrogel-forming polymer is selected from the group consisting of polysaccharides, water soluble polyacrylates, polyphosphazenes, poly(acrylic acids), poly(methacrylic acids), copolymers of acrylic acid and methacrylic acid, poly(alkylene oxides), poly(vinyl acetate), polyvinylpyrrolidones, and blends thereof.

6. The population of hydrogel capsules of claim 5, wherein the biocompatible, hydrogel-forming polymer is selected from the group consisting of polysaccharides, polyphosphazenes, poly(alkylene oxides), poly(vinyl acetates), polyvinylpyrrolidones, and blends thereof.

7. The population of hydrogel capsules of claim 5, wherein the biocompatible, hydrogel-forming polymer is a polysaccharide selected from the group consisting of alginate, chitosan, hyaluronan, and chondroitin sulfate.

8. The population of hydrogel capsules of claim 7, wherein the polysaccharide is an alginate.

9. The population of hydrogel capsules of claim 8, wherein the alginate is cross-linked with barium divalent ions.

10. The population of hydrogel capsules of claim 1, wherein the mean diameter is at least 1.2 mm and less than 8 mm and the hydrogel capsules encapsulating the mammalian cells consist of two hydrogel layers: the inner hydrogel layer comprising the mammalian cells and the second outer, cell-free hydrogel layer.

11. The population of hydrogel capsules of claim 10, wherein the mean diameter is between 1.5 mm and 2 mm.

12. The population of hydrogel capsules of claim 10, wherein the biocompatible, hydrogel-forming polymer in the second outer, cell-free hydrogel layer comprises an alginate.

13. The population of hydrogel capsules of claim 12, wherein the biocompatible, hydrogel-forming polymer in the first inner, hydrogel layer comprises an alginate.

14. The population of hydrogel capsules of claim 12, wherein the second outer, cell-free hydrogel layer comprises an anti-inflammatory drug or a diagnostic agent.

15. The population of hydrogel capsules of claim 1, wherein the mammalian cells are human cells.

16. The population of hydrogel capsules of claim 1, wherein the mammalian cells secrete a therapeutically effective substance.

17. The population of hydrogel capsules of claim 1, wherein the mammalian cells are genetically engineered.

18. The population of hydrogel capsules of claim 16, wherein the therapeutically effective substance is a hormone, a growth factor, a blood clotting factor, or an enzyme.

19. A method of providing functional cells to an individual in need thereof comprising transplanting or injecting into the individual an effective amount of a population of hydrogel capsules of claim 1.

20. A population of hydrogel capsules consisting essentially of hydrogel capsules that have a mean diameter, as measured by confocal microscopy, of at least 1.2 mm and less than 3 mm, wherein the hydrogel capsules:
   (i) encapsulate genetically engineered mammalian cells;
   (ii) consist of two hydrogel layers and an optional acellular core as a third layer, and wherein the two hydrogel layers contain a first inner, hydrogel layer comprising the genetically engineered mammalian cells, and a second outer, cell-free hydrogel layer, and wherein the first and second hydrogel layers independently have a three-dimensional open-lattice polymeric structure formed by crosslinking of a biocompatible hydrogel-forming polymer; and
   (iii) are spheres or ellipsoids having semi-principal axes within 10% of each other.

* * * * *